US011866741B2

(12) United States Patent
Olejnik et al.

(10) Patent No.: US 11,866,741 B2
(45) Date of Patent: Jan. 9, 2024

(54) POLYMERASE ENZYME FROM 9°N

(71) Applicant: IsoPlexis Corporation, Branford, CT (US)

(72) Inventors: Jerzy Olejnik, Brookline, MA (US); Angela Delucia, Cambridge, MA (US)

(73) Assignee: IsoPlexis Corporation, Branford, CT (US)

( * ) Notice: Subject to any disclaimer, the term of this patent is extended or adjusted under 35 U.S.C. 154(b) by 71 days.

(21) Appl. No.: 17/350,078

(22) Filed: Jun. 17, 2021

(65) Prior Publication Data

US 2021/0317423 A1    Oct. 14, 2021

Related U.S. Application Data

(63) Continuation of application No. 16/485,279, filed as application No. PCT/US2018/018004 on Feb. 13, 2018, now abandoned.

(60) Provisional application No. 62/458,404, filed on Feb. 13, 2017.

(30) Foreign Application Priority Data

Mar. 10, 2017   (EP) ..................... 17160392

(51) Int. Cl.
| C12N 9/12 | (2006.01) |
| C12Q 1/6848 | (2018.01) |
| C12Q 1/6844 | (2018.01) |
| C12Q 1/6869 | (2018.01) |

(52) U.S. Cl.
CPC ......... *C12N 9/1252* (2013.01); *C12Q 1/6844* (2013.01); *C12Q 1/6869* (2013.01); *C12Y 207/07007* (2013.01)

(58) Field of Classification Search
CPC ......... C12N 9/12; C12N 9/1252; C12P 19/34; C12Q 1/6844; C12Q 1/6869; C12Y 207/07007
See application file for complete search history.

(56) References Cited

U.S. PATENT DOCUMENTS

| 5,412,414 A | 5/1995 | Ast et al. |
| 5,756,334 A | 5/1998 | Perler et al. |
| 6,946,273 B1 * | 9/2005 | Sorge .................. B82Y 5/00 424/94.5 |
| 7,045,328 B2 | 5/2006 | Mathur |
| 8,268,605 B2 | 9/2012 | Sorge et al. |
| 8,283,148 B2 | 10/2012 | Sorge et al. |
| 8,349,600 B2 | 1/2013 | Martin et al. |
| 8,367,376 B2 | 2/2013 | Vander et al. |
| 8,435,775 B2 | 5/2013 | Holliger et al. |
| 8,460,910 B2 | 6/2013 | Smith et al. |
| 8,557,554 B2 | 10/2013 | Connolly et al. |
| 8,623,628 B2 | 1/2014 | Ost et al. |
| 8,772,006 B2 * | 7/2014 | Sorge .................. B82Y 5/00 435/194 |
| 8,921,044 B2 | 12/2014 | Gardner |
| 9,040,276 B2 | 5/2015 | Borns |
| 9,085,762 B2 | 7/2015 | Hogrefe et al. |
| 9,181,534 B1 | 11/2015 | Hogrefe et al. |
| 9,267,130 B2 | 2/2016 | Martin et al. |
| 9,273,352 B2 | 3/2016 | Smith et al. |
| 9,322,050 B2 | 4/2016 | Olejnik |
| 9,469,862 B2 | 10/2016 | Chaput et al. |
| 9,677,057 B2 | 6/2017 | Bomati et al. |
| 9,765,309 B2 | 9/2017 | Chen et al. |
| 9,834,762 B2 | 12/2017 | Chaput et al. |
| 9,902,993 B2 | 2/2018 | Fredriksson et al. |
| 10,059,928 B2 | 8/2018 | Smith et al. |
| 10,421,996 B2 | 9/2019 | Bomati et al. |
| 10,577,593 B2 | 3/2020 | Vander et al. |
| 10,662,413 B2 | 5/2020 | Lin et al. |
| 10,745,751 B2 | 8/2020 | Bomati et al. |
| 10,870,836 B2 | 12/2020 | Chen et al. |
| 2003/0228616 A1 | 12/2003 | Arezi et al. |
| 2005/0069908 A1 | 3/2005 | Sorge et al. |
| 2006/0240439 A1 | 10/2006 | Smith et al. |
| 2007/0048748 A1 | 3/2007 | Williams et al. |
| 2007/0190538 A1 | 8/2007 | Martin et al. |
| 2008/0280291 A1 | 11/2008 | Sorge et al. |
| 2011/0045489 A1 | 2/2011 | Gardner et al. |
| 2013/0196327 A1 | 8/2013 | Gardner |
| 2014/0234940 A1 | 8/2014 | Peris et al. |
| 2015/0376582 A1 | 12/2015 | Chen et al. |
| 2020/0002689 A1 | 1/2020 | Olejnik et al. |

(Continued)

FOREIGN PATENT DOCUMENTS

| EP | 1350841 A2 | 10/2003 |
| JP | 2004500052 A | 1/2004 |

(Continued)

OTHER PUBLICATIONS

Arezi, B. et, al., (2002) "Efficient and High Fidelity Incorporation of Dye-terminators by a Novel Archaeal DNA Polymerase Mutant," J Mal. Biol. 322(4), 719-729.

Braithwaite and Ito, "Compilation, alignment, and phylogenetic relationships of DNA polymerases", Nucleic Acids Research, 1993, vol. 21, No. 4, p. 787-802.

Certificate of Analysis from New England Biolabs for Therminator™ II DNA PolymeraseM0266S, No. Date, 2 pages.

(Continued)

*Primary Examiner* — Maryam Monshipouri
(74) *Attorney, Agent, or Firm* — COOLEY LLP; Ivor R. Elrifi; Andrew R. Henderson

(57) ABSTRACT

The present invention relates to a polymerase enzyme from 9° N with improved ability to incorporate reversibly terminating nucleotides. The enzyme comprising mutations in the motif A region. The invention also relates to methods of using such enzymes as well as a kit with such polymerases.

12 Claims, 11 Drawing Sheets

Specification includes a Sequence Listing.

(56) References Cited

U.S. PATENT DOCUMENTS

| | | |
|---|---|---|
| 2020/0231947 A1 | 7/2020 | Peist et al. |
| 2021/0254032 A1 | 8/2021 | Peist et al. |
| 2022/0127587 A1 | 4/2022 | Olejnik et al. |
| 2022/0145272 A1 | 5/2022 | Olejnik et al. |
| 2022/0177859 A1 | 6/2022 | Olejnik et al. |

FOREIGN PATENT DOCUMENTS

| | | |
|---|---|---|
| JP | 2007504817 A | 3/2007 |
| JP | 2008539750 A | 11/2008 |
| WO | WO-9844151 A1 | 10/1998 |
| WO | WO-9844152 A1 | 10/1998 |
| WO | WO-0006770 A1 | 2/2000 |
| WO | WO-0018957 A1 | 4/2000 |
| WO | WO-0123411 A2 | 4/2001 |
| WO | WO-0138546 A1 | 5/2001 |
| WO | WO-0157248 A2 | 8/2001 |
| WO | WO-03054139 A2 | 7/2003 |
| WO | WO-2004018497 A2 | 3/2004 |
| WO | WO-2005024010 A1 | 3/2005 |
| WO | WO-2006030174 A1 | 3/2006 |
| WO | WO-2008083393 A2 | 7/2008 |
| WO | WO-2009131919 A2 | 10/2009 |
| WO | WO-2010141390 A2 | 12/2010 |
| WO | WO-2010141391 A2 | 12/2010 |
| WO | WO-2012154934 A1 | 11/2012 |
| WO | WO-2014142921 A1 | 9/2014 |
| WO | WO-2017042040 A1 | 3/2017 |
| WO | WO-2017079498 A2 | 5/2017 |
| WO | WO-2018148723 A1 | 8/2018 |
| WO | WO-2018148724 A1 | 8/2018 |
| WO | WO-2018148726 A1 | 8/2018 |
| WO | WO-2018148727 A1 | 8/2018 |

OTHER PUBLICATIONS

Chen, C.Y et, al., (2014) "DNA Polymerases Drive DNA Sequencing-by-Synthesis Technologies: Both Past and Present," Frontiers in Microbiology 5, 11 pages.

Cheng et al., "Directed evolution 2.0: improving and deciphering enzyme properties", Chem. Commun. 2015, vol. 51, No. 48, p. 9760-9772.

Database accession No. BBN98964 sequence, "Pyrococcus furiosus exo polymerase protein, SEQ: 18", retrieved from EBI accession No. GSP:BBN98964, Nov. 6, 2014.

Database accession No. BCK66907 sequence, 11 Pyrococcus sp. DNA polymerase mutant K477M/L408AN409A/P410X, SEQ ID 19., retrieved from EBI accession No. GSP:BCK66907, Feb. 25, 2016, 2 p.

Evans, et al., Improving dideoxynucleotide-triphosphate utilisation by the hyper-thermophilic DNA polymerase from the archaeon Pyrococcus furiosus, Nucleic Acids Research, 2000, pp. 1059-1066.

Unknown Author, "Polymerase Report", Experimental report on incorporation of reversibly terminated fluorescent nucleotides by SGS polymerase variants as compared to other sequencing polymerases, Apr. 2022, 8 pages.

Federal Register at vol. 64, No. 244, Dec. 21, 1999, pp. 71427-71440.

Frey et al., "Construction and characterization of a bacteriophage T4 DNA polymerase deficient in 3-5 exonuclease activity" Proc. Natl. Acad. Sci. USA. vol. 90, 1993. pp. 2579-2583.

Gardner, et al. "Acyclic and dideoxy terminator preferences denote divergent sugar recognition by archaean and Taq DNA polymerases", Nucleic Acids Research, Information Retrieval Ltd, vol. 30, No. 2, (2002), pp. 605-613.

Gardner et al., "Determinants of nucleotide sugar recognition in an archaeon DNA polymerase," Nucleic Acids Research, vol. 27, No. 12, (1999), p. 2545-2553.

International Preliminary Report on Patentability dated Aug. 13, 2019 by the International Searching Authority for International Application No. PCT/US2018/018004, filed on Feb. 13, 2018 and published as WO 2018/148727 on Aug. 16, 2018, 15 pages.

International Search Report and Written Opinion dated Jul. 10, 2018 by the International Searching Authority for International Application No. PCT/US2018/018004, filed on Feb. 13, 2018 and published as WO 2018/148727 on Aug. 16, 2018, 21 pages.

Lee et al. ": Fluorescent in situ sequencing (FISSEQ) of RNA for gene expression profiling in intact cells and tissues", Nature Protocols vol. 10, No. 3, (2015), p. 442- 458.

Mitra, Robi D., et al. "Fluorescent in situ sequencing on polymerase colonies." Analytical Biochemistry 320.1 (2003): 55-65.

Ngo et al. in The Protein Folding Problem and Tertiary Structure Prediction, 1994, Merz et al. (ed.), Birkhauser, Boston, MA, p. 433 and 492-495.

Pfu DNA polymerase from Wikipedia, printed on Sep. 2, 2022, 3 pages.

Firebird Biomolecular Sciences, LLC, Product information for Firebird reversibly terminated nucleotides, 2021, 2 pages.

Reha-Krantz et al., "Motif A of Bacteriophage T4 DNA Polymerase: Role in Primer Extension and DNA Replication Fidelity. Isolation of new anti mutator and mutator DNA polymerases", J. Biol. Chem. 269:5635-5643, 1994 (Year: 1994).

Schultz et al., Proteins Structure and Function, pp. 521-528, Plenum Press, New York, 1987 (Year: 1987).

Singh et al., "Protein Engineering Approaches in the Post-Genomic Era" Current Protein and Peptide Science, 2017, 18, 1-11.

Southworth, et al., Cloning of thermostable DNA polymerases from hyperthermophilic marine Archaea with emphasis on Thermococcus sp. 9 degrees N-7 and mutations affecting 3'-5' exonuclease activity, Proceedings of the National Academy of Sciences of the United States of America, 1996, pp. 5281-5285.

Spicer, et a., Primary structure of T4 DNA polymerase. Evolutionary relatedness to eucaryotic and other prokaryotic DNA polymerases, J Biol Chem. Jun. 1988, pp. 7478-7486.

Stratagene Catalog (1988), p. 39. Published by Stratgene, 11011 North Torrey Pines Road, La Jolla, CA 92037, USA.

Tabor, et al., A single residue in DNA polymerases of the Escherichia coli DNA polymerase I family is critical for distinguishing between deoxy- and dideoxyribonucleotides, Proceedings of the National Academy of Sciences of the United States of America, 1995, pp. 6339-6343.

Therminator™ DNA Polymerase M0261S; Product information, Dec. 17, 2022, 3 pages.

UniProtKB-056366 (DPOL_THES9); downloaded Nov. 18, 2020 from the www.uniprot.org/uniprot/Q56366, pp. 1-4.

Vander Horn et al. "ThermoSequenaseTM DNA Polymerase and T. acidophilum Pyrophosphatase: New Thermostable Enzymes for DNA Sequencing", BioTechniques, vol. 22, (1997), p. 758-765.

Yu et al. "Fluorescence-based, high-throughput DNA polymerase assay", BioTechniques, vol. 33, (2002), p. 938-941.

Zhang et al.: "Archaeal DNA polymerases in biotechnology", Applied Microbiology and Biotechnology, vol. 99, No. 16, (2015), p. 6585-6597.

Zhang et al., "Propagated Perturbations from a Peripheral Mutation Show Interactions Supporting WW Domain Thermostability" Structure 26, 2016.1474-1485.

Communication of Notices of Opposition dated Sep. 1, 2021 filed against European Application EP18706946.3 (Patent No. 3580350); 3 pages.

Communication of a Notice of Opposition dated Aug. 20, 2021 filed against European Application EP18706946.3 (Patent No. 3580350); 28 pages.

Decision to Discontinue the Opposition Proceedings dated Oct. 4, 2022 filed against European Application EP18706946.3 (Patent No. 3580350); 2 pages.

Opposition documents dated Aug. 17, 2021 filed against European Application EP18706946.3 (Patent No. 3580350); Patentee: Qiagen Sciences, LLC; Opponent: Maiwald Patentanwalts; 29 pages.

Submission in Opposition Proceedings dated May 11, 2022 filed against European Application EP18706946.3 (Patent No. 3580350); 63 pages.

Withdrawal of Opposition dated Sep. 21, 2022 filed against European Application EP18706946.3 (Patent No. 3580350); 3 pages.

* cited by examiner

101xGP      min coverage 200x

| GR | Sample | Type | Total length of target region | True pos | False neg | False pos | True neg |
|---|---|---|---|---|---|---|---|
| 6.7 | MR12 | T9 baseline | 28,771 | 17 | 2 | 137 | 28,615 |
| 6.7 | MR12 | T9 baseline | 28,689 | 18 | 1 | 160 | 28,510 |
| 6.7 | MR12 | Jpol5 | 30,432 | 20 | 0 | 32 | 30,380 |
| 6.7 | MR12 | Jpol5 | 31,705 | 20 | 0 | 32 | 31,653 |
| 6.7 | MR12 | Jpol8 | 31,745 | 20 | 0 | 31 | 31,694 |
| 6.7 | MR12 | Jpol8 | 31,322 | 20 | 0 | 31 | 31,271 |
| 6.15 | MR12 | T9 baseline | 32,161 | 20 | 0 | 86 | 32,054 |
| 6.15 | MR12 | T9 baseline | 31,952 | 20 | 0 | 83 | 31,849 |
| 6.15 | MR12 | Jpol5 | 33,678 | 21 | 0 | 28 | 33,629 |
| 6.15 | MR12 | Jpol5 | 33,698 | 21 | 0 | 26 | 33,651 |
| 6.15 | MR12 | Jpol8 | 33,929 | 21 | 0 | 26 | 33,883 |
| 6.15 | MR12 | Jpol8 | 33,327 | 21 | 0 | 27 | 33,280 |

FIG. 5

SEQUENCE LISTING

<160> NUMBER OF SEQ ID NOS: 20

<210> SEQ ID NO 1
<211> LENGTH: 771
<212> TYPE: PRT
<213> ORGANISM: Thermococcus sp.

<400> SEQUENCE: 1

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Thr Met Leu Ala Phe Asp Ile Glu Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365

-continued

Pro Asn Lys Pro Asp Glu Arg Glu Leu Ala Arg Arg Gly Gly Tyr
370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Thr His
            405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
450                 455                 460

Arg Lys Met Lys Ala Thr Val Asp Pro Leu Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Val
770

```
<210> SEQ ID NO 2
<211> LENGTH: 775
<212> TYPE: PRT
<213> ORGANISM: Thermococcus sp.

<400> SEQUENCE: 2

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Thr Met Leu Ala Phe Ala Ile Ala Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Ala Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
    370                 375                 380
```

Ala Gly Gly Tyr Val Lys Glu Pro Glu Arg Gly Leu Trp Asp Asn Ile
385                 390                 395                 400

Val Tyr Leu Asp Phe Arg Ser Ser Gly Ser Ser Ile Ile Ile Thr His
        405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
                435                 440                 445

Ile Pro Ser Leu Leu Gly Asp Leu Leu Glu Glu Arg Gln Lys Ile Lys
            450                 455                 460

Arg Lys Met Lys Ala Thr Val Asp Pro Leu Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
        500                 505                 510

Val Thr Ala Trp Gly Arg Glu Tyr Ile Glu Met Val Ile Arg Glu Leu
            515                 520                 525

Glu Glu Lys Phe Gly Phe Lys Val Leu Tyr Ala Asp Thr Asp Gly Leu
530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Val Lys Gly Lys Lys
        770                 775

<210> SEQ ID NO 3
<211> LENGTH: 775
<212> TYPE: PRT

<213> ORGANISM: Thermococcus sp.

<400> SEQUENCE: 3

```
Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Thr Met Leu Ala Phe Ala Ile Ala Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
    370                 375                 380

Ala Gly Gly Tyr Val Lys Glu Pro Glu Arg Gly Leu Trp Asp Asn Ile
385                 390                 395                 400
```

```
Val Tyr Leu Asp Phe Arg Ser Ser Gly Ser Ile Ile Ile Thr His
            405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
            435                 440                 445

Ile Pro Ser Leu Leu Gly Asp Leu Leu Glu Glu Arg Gln Lys Ile Lys
            450                 455                 460

Arg Lys Met Lys Ala Thr Val Asp Pro Leu Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
            515                 520                 525

Glu Glu Lys Phe Gly Phe Lys Val Leu Tyr Ala Asp Thr Asp Gly Leu
            530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
            595                 600                 605

Glu Ile Val Arg Arg Asp Trp Ser Glu Ile Ala Lys Glu Thr Gln Ala
610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
            690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
            755                 760                 765

Leu Lys Val Lys Gly Lys Lys
770                 775

<210> SEQ ID NO 4
<211> LENGTH: 775
<212> TYPE: PRT
<213> ORGANISM: Thermococcus sp.

<400> SEQUENCE: 4
```

```
Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Thr Met Leu Ala Phe Ala Ile Ala Thr
130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Cys Glu
210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
370                 375                 380

Ala Gly Gly Tyr Val Lys Glu Pro Glu Arg Gly Leu Trp Asp Asn Ile
385                 390                 395                 400

Val Tyr Leu Asp Phe Arg Ser His Thr Cys Ser Ile Ile Ile Thr His
            405                 410                 415
```

```
Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Arg Lys Met Lys Ala Thr Val Asp Pro Leu Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Val Lys Gly Lys Lys
    770                 775

<210> SEQ ID NO 5
<211> LENGTH: 775
<212> TYPE: PRT
<213> ORGANISM: Thermococcus sp.

<400> SEQUENCE: 5

Met Ile Leu Asp Thr Asp Tyr Ile Thr Glu Asn Gly Lys Pro Val Ile
1               5                   10                  15
```

```
Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
 50                  55                  60

Val Lys Arg Ala Glu Lys Val Gln Lys Lys Phe Leu Gly Arg Pro Ile
 65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
                100                 105                 110

Asp Ile Pro Phe Ala Lys Arg Tyr Leu Ile Asp Lys Gly Leu Ile Pro
            115                 120                 125

Met Glu Gly Asp Glu Glu Leu Thr Met Leu Ala Phe Ala Ile Ala Thr
130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Met Thr Cys Ser Ile Ile Thr His
                405                 410                 415

Asn Val Ser Pro Asp Thr Leu Asn Arg Glu Gly Cys Lys Glu Tyr Asp
            420                 425                 430
```

```
Val Ala Pro Glu Val Gly His Lys Phe Cys Lys Asp Phe Pro Gly Phe
            435                 440                 445

Ile Pro Ser Leu Leu Gly Asp Leu Leu Glu Glu Arg Gln Lys Ile Lys
        450                 455                 460

Arg Lys Met Lys Ala Thr Val Asp Pro Leu Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Val Lys Gly Lys Lys
770                 775

<210> SEQ ID NO 6
<211> LENGTH: 775
<212> TYPE: PRT
<213> ORGANISM: Thermococcus sp.

<400> SEQUENCE: 6

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30
```

```
Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
 50                  55                  60

Val Lys Arg Ala Glu Lys Val Gln Lys Lys Phe Leu Gly Arg Pro Ile
 65                  70                  75                  80

Glu Val Trp Lys Leu Tyr Phe Asn His Pro Gln Asp Val Pro Ala Ile
                 85                  90                  95

Arg Asp Arg Ile Arg Ala His Pro Ala Val Val Asp Ile Tyr Glu Tyr
                100                 105                 110

Asp Ile Pro Phe Ala Lys Arg Tyr Leu Ile Asp Lys Gly Leu Ile Pro
                115                 120                 125

Met Glu Gly Asp Glu Glu Leu Thr Met Leu Ala Phe Ala Ile Ala Thr
        130                 135                 140

Leu Tyr His Glu Gly Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Ser Thr Glu Lys Glu Met Ile Lys
                180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Cys Glu
210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
                260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
        290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
                340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Tyr
        370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Gly Thr Phe Ser Ile Ile Ile Thr His
                405                 410                 415

Asn Val Ser Pro Asp Thr Leu Asn Arg Glu Gly Cys Lys Glu Tyr Asp
                420                 425                 430

Val Ala Pro Glu Val Gly His Lys Phe Cys Lys Asp Phe Pro Gly Phe
        435                 440                 445
```

```
Ile Pro Ser Leu Leu Gly Asp Leu Glu Glu Arg Gln Lys Ile Lys
    450                 455                 460

Arg Lys Met Lys Ala Thr Val Asp Pro Leu Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Val Lys Gly Lys Lys
    770                 775

<210> SEQ ID NO 7
<211> LENGTH: 775
<212> TYPE: PRT
<213> ORGANISM: Thermococcus sp.

<400> SEQUENCE: 7

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45
```

-continued

Glu Asp Val Lys Lys Val Thr Ala Lys Arg His Gly Thr Val Val Lys
 50                  55                  60

Val Lys Arg Ala Glu Lys Val Gln Lys Lys Phe Leu Gly Arg Pro Ile
 65                  70                  75                  80

Glu Val Trp Lys Leu Tyr Phe Asn His Pro Gln Asp Val Pro Ala Ile
                 85                  90                  95

Arg Asp Arg Ile Arg Ala His Pro Ala Val Val Asp Ile Tyr Glu Tyr
                100                 105                 110

Asp Ile Pro Phe Ala Lys Arg Tyr Leu Ile Asp Lys Gly Leu Ile Pro
            115                 120                 125

Met Glu Gly Asp Glu Leu Thr Met Leu Ala Phe Ala Ile Ala Thr
130                 135                 140

Leu Tyr His Glu Gly Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
                180                 185                 190

Arg Phe Leu Arg Val Val Arg Glu Lys Asp Pro Asp Val Leu Ile Thr
    195                 200                 205

Tyr Asn Gly Asp Asn Phe Asp Phe Ala Tyr Leu Lys Lys Arg Cys Glu
210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
                260                 265                 270

Tyr Thr Leu Glu Ala Val Tyr Glu Ala Val Phe Gly Lys Pro Lys Glu
            275                 280                 285

Lys Val Tyr Ala Glu Glu Ile Ala Gln Ala Trp Glu Ser Gly Glu Gly
        290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Gly Thr Cys Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
450                 455                 460

```
Arg Lys Met Lys Ala Thr Val Asp Pro Leu Glu Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
                515                 520                 525

Glu Glu Lys Phe Gly Phe Lys Val Leu Tyr Ala Asp Thr Asp Gly Leu
                530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
                580                 585                 590

Lys Tyr Ala Val Ile Asp Glu Glu Gly Lys Ile Thr Thr Arg Gly Leu
                595                 600                 605

Glu Ile Val Arg Arg Asp Trp Ser Glu Ile Ala Lys Glu Thr Gln Ala
610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
                660                 665                 670

Tyr Lys Ala Thr Gly Pro His Val Ala Val Ala Lys Arg Leu Ala Ala
                675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
                740                 745                 750

Glu Asp Leu Arg Tyr Gln Lys Thr Lys Gln Val Gly Leu Gly Ala Trp
                755                 760                 765

Leu Lys Val Lys Gly Lys
770                 775

<210> SEQ ID NO 8
<211> LENGTH: 775
<212> TYPE: PRT
<213> ORGANISM: Thermococcus sp.

<400> SEQUENCE: 8

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
50                  55                  60
```

```
Val Lys Arg Ala Glu Lys Val Gln Lys Lys Phe Leu Gly Arg Pro Ile
 65                  70                  75                  80

Glu Val Trp Lys Leu Tyr Phe Asn His Pro Gln Asp Val Pro Ala Ile
                 85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Thr Met Leu Ala Phe Ala Ile Ala Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Cys Glu
210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Arg Gly Gly Tyr
370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Asn Thr Cys Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Arg Lys Met Lys Ala Thr Val Asp Pro Leu Glu Lys Lys Leu Leu Asp
465                 470                 475                 480
```

```
Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
            515                 520                 525

Glu Glu Lys Phe Gly Phe Lys Val Leu Tyr Ala Asp Thr Asp Gly Leu
            530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
                580                 585                 590

Lys Tyr Ala Val Ile Asp Glu Glu Gly Lys Ile Thr Thr Arg Gly Leu
                595                 600                 605

Glu Ile Val Arg Arg Asp Trp Ser Glu Ile Ala Lys Glu Thr Gln Ala
                610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
                660                 665                 670

Tyr Lys Ala Thr Gly Pro His Val Ala Val Ala Lys Arg Leu Ala Ala
                675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
                740                 745                 750

Glu Asp Leu Arg Tyr Gln Lys Thr Lys Gln Val Gly Leu Gly Ala Trp
                755                 760                 765

Leu Lys Val Lys Gly Lys Lys
                770                 775

<210> SEQ ID NO 9
<211> LENGTH: 775
<212> TYPE: PRT
<213> ORGANISM: Thermococcus sp.

<400> SEQUENCE: 9

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
        50                  55                  60

Val Lys Arg Ala Glu Lys Val Gln Lys Lys Phe Leu Gly Arg Pro Ile
65                  70                  75                  80
```

```
Glu Val Trp Lys Leu Tyr Phe Asn His Pro Gln Asp Val Pro Ala Ile
            85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
            115                 120                 125

Met Glu Gly Asp Glu Glu Leu Thr Met Leu Ala Phe Ala Ile Ala Thr
130                 135                 140

Leu Tyr His Glu Gly Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
            165                 170                 175

Asp Leu Pro Tyr Val Asp Val Ser Thr Glu Lys Glu Met Ile Lys
            180                 185                 190

Arg Phe Leu Arg Val Val Arg Glu Lys Asp Pro Asp Val Leu Ile Thr
            195                 200                 205

Tyr Asn Gly Asp Asn Phe Asp Phe Ala Tyr Leu Lys Lys Arg Cys Glu
            210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
                260                 265                 270

Tyr Thr Leu Glu Ala Val Tyr Glu Ala Val Phe Gly Lys Pro Lys Glu
            275                 280                 285

Lys Val Tyr Ala Glu Glu Ile Ala Gln Ala Trp Glu Ser Gly Glu Gly
290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
            325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
            355                 360                 365

Pro Asn Lys Pro Asp Glu Arg Glu Leu Ala Arg Arg Arg Gly Gly Tyr
370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Gly Thr Asn Ser Ile Ile Ile Thr His
            405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
            435                 440                 445

Ile Pro Ser Leu Leu Gly Asp Leu Leu Glu Glu Arg Gln Lys Ile Lys
450                 455                 460

Arg Lys Met Lys Ala Thr Val Asp Pro Leu Glu Lys Lys Leu Leu Asp
465                 470                 475                 480

Tyr Arg Gln Arg Leu Ile Lys Ile Leu Ala Asn Ser Phe Tyr Gly Tyr
            485                 490                 495
```

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Val Lys Gly Lys Lys
    770                 775

<210> SEQ ID NO 10
<211> LENGTH: 775
<212> TYPE: PRT
<213> ORGANISM: Thermococcus sp.

<400> SEQUENCE: 10

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Phe Leu Gly Arg Pro Ile
65                  70                  75                  80

Glu Val Trp Lys Leu Tyr Phe Asn His Pro Gln Asp Val Pro Ala Ile
                85                  90                  95

-continued

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
            115                 120                 125

Met Glu Gly Asp Glu Glu Leu Thr Met Leu Ala Phe Ala Ile Ala Thr
130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
            195                 200                 205

Tyr Asn Gly Asp Asn Phe Asp Phe Ala Tyr Leu Lys Lys Arg Cys Glu
210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
            275                 280                 285

Lys Val Tyr Ala Glu Glu Ile Ala Gln Ala Trp Glu Ser Gly Glu Gly
290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
            355                 360                 365

Pro Asn Lys Pro Asp Glu Arg Glu Leu Ala Arg Arg Arg Gly Gly Tyr
370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Thr Thr Cys Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
            435                 440                 445

Ile Pro Ser Leu Leu Gly Asp Leu Leu Glu Glu Arg Gln Lys Ile Lys
450                 455                 460

Arg Lys Met Lys Ala Thr Val Asp Pro Leu Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

```
Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
            565                 570                 575

Leu Glu Tyr Glu Gly Phe Tyr Val Arg Gly Phe Phe Val Thr Lys Lys
        580                 585                 590

Lys Tyr Ala Val Ile Asp Glu Glu Gly Lys Ile Thr Thr Arg Gly Leu
    595                 600                 605

Glu Ile Val Arg Arg Asp Trp Ser Glu Ile Ala Lys Glu Thr Gln Ala
610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
            645                 650                 655

Pro Glu Lys Leu Val Ile His Glu Gln Ile Thr Arg Asp Leu Arg Asp
        660                 665                 670

Tyr Lys Ala Thr Gly Pro His Val Ala Val Ala Lys Arg Leu Ala Ala
    675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
            725                 730                 735

Val Leu Pro Ala Val Glu Arg Ile Leu Lys Ala Phe Gly Tyr Arg Lys
        740                 745                 750

Glu Asp Leu Arg Tyr Gln Lys Thr Lys Gln Val Gly Leu Gly Ala Trp
    755                 760                 765

Leu Lys Val Lys Gly Lys Lys
770                 775

<210> SEQ ID NO 11
<211> LENGTH: 775
<212> TYPE: PRT
<213> ORGANISM: Thermococcus sp.

<400> SEQUENCE: 11

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110
```

```
Asp Ile Pro Phe Ala Lys Arg Tyr Leu Ile Asp Lys Gly Leu Ile Pro
        115                 120                 125

Met Glu Gly Asp Glu Glu Leu Thr Met Leu Ala Phe Ala Ile Ala Thr
130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
                180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser His Val Cys Ser Ile Ile Thr His His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Arg Lys Met Lys Ala Thr Val Asp Pro Leu Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525
```

```
Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Val Lys Gly Lys Lys
    770                 775

<210> SEQ ID NO 12
<211> LENGTH: 775
<212> TYPE: PRT
<213> ORGANISM: Thermococcus sp.

<400> SEQUENCE: 12

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125
```

```
Met Glu Gly Asp Glu Glu Leu Thr Met Leu Ala Phe Ala Ile Ala Thr
    130                 135                 140
Leu Tyr His Glu Gly Glu Phe Gly Thr Gly Pro Ile Leu Met Ile
145                 150                 155                 160
Ser Tyr Ala Asp Gly Ser Glu Ala Arg Val Ile Thr Trp Lys Lys Ile
                165                 170                 175
Asp Leu Pro Tyr Val Asp Val Ser Thr Glu Lys Glu Met Ile Lys
            180                 185                 190
Arg Phe Leu Arg Val Val Arg Glu Lys Asp Pro Asp Val Leu Ile Thr
        195                 200                 205
Tyr Asn Gly Asp Asn Phe Asp Phe Ala Tyr Leu Lys Lys Arg Cys Glu
    210                 215                 220
Glu Leu Gly Ile Lys Phe Thr Leu Gly Arg Asp Gly Ser Glu Pro Lys
225                 230                 235                 240
Ile Gln Arg Met Gly Asp Arg Phe Ala Val Glu Val Lys Gly Arg Ile
                245                 250                 255
His Phe Asp Leu Tyr Pro Val Ile Arg Arg Thr Ile Asn Leu Pro Thr
            260                 265                 270
Tyr Thr Leu Glu Ala Val Tyr Glu Ala Val Phe Gly Lys Pro Lys Glu
        275                 280                 285
Lys Val Tyr Ala Glu Glu Ile Ala Gln Ala Trp Glu Ser Gly Glu Gly
    290                 295                 300
Leu Glu Arg Val Ala Arg Tyr Ser Met Glu Asp Ala Lys Val Thr Tyr
305                 310                 315                 320
Glu Leu Gly Arg Glu Phe Phe Pro Met Glu Ala Gln Leu Ser Arg Leu
                325                 330                 335
Ile Gly Gln Ser Leu Trp Asp Val Ser Arg Ser Ser Thr Gly Asn Leu
            340                 345                 350
Val Glu Trp Phe Leu Leu Arg Lys Ala Tyr Lys Arg Asn Glu Leu Ala
        355                 360                 365
Pro Asn Lys Pro Asp Glu Arg Glu Leu Ala Arg Arg Arg Gly Gly Tyr
    370                 375                 380
Ala Gly Gly Tyr Val Lys Glu Pro Glu Arg Gly Leu Trp Asp Asn Ile
385                 390                 395                 400
Val Tyr Leu Asp Phe Arg Ser Met Val Cys Ser Ile Ile Thr His
                405                 410                 415
Asn Val Ser Pro Asp Thr Leu Asn Arg Glu Gly Cys Lys Glu Tyr Asp
            420                 425                 430
Val Ala Pro Glu Val Gly His Lys Phe Cys Lys Asp Phe Pro Gly Phe
        435                 440                 445
Ile Pro Ser Leu Leu Gly Asp Leu Leu Glu Glu Arg Gln Lys Ile Lys
    450                 455                 460
Arg Lys Met Lys Ala Thr Val Asp Pro Leu Glu Lys Lys Leu Leu Asp
465                 470                 475                 480
Tyr Arg Gln Arg Leu Ile Lys Ile Leu Ala Asn Ser Phe Tyr Gly Tyr
                485                 490                 495
Tyr Gly Tyr Ala Lys Ala Arg Trp Tyr Cys Lys Glu Cys Ala Glu Ser
            500                 505                 510
Val Thr Ala Trp Gly Arg Glu Tyr Ile Glu Met Val Ile Arg Glu Leu
        515                 520                 525
Glu Glu Lys Phe Gly Phe Lys Val Leu Tyr Ala Asp Thr Asp Gly Leu
    530                 535                 540
```

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Val Lys Gly Lys Lys
770                 775

<210> SEQ ID NO 13
<211> LENGTH: 775
<212> TYPE: PRT
<213> ORGANISM: Thermococcus sp.

<400> SEQUENCE: 13

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
        50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Thr Met Leu Ala Phe Ala Ile Ala Thr
130                 135                 140

```
Leu Tyr His Glu Gly Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Thr Val Cys Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Arg Lys Met Lys Ala Thr Val Asp Pro Leu Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560
```

```
Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Val Lys Gly Lys Lys
    770                 775

<210> SEQ ID NO 14
<211> LENGTH: 775
<212> TYPE: PRT
<213> ORGANISM: Thermococcus sp.

<400> SEQUENCE: 14

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Thr Met Leu Ala Phe Ala Ile Ala Thr
    130                 135                 140

Leu Tyr His Glu Gly Glu Glu Phe Gly Thr Gly Pro Ile Leu Met Ile
145                 150                 155                 160
```

Ser Tyr Ala Asp Gly Ser Glu Ala Arg Val Ile Thr Trp Lys Lys Ile
            165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
            195                 200                 205

Tyr Asn Gly Asp Asn Phe Asp Phe Ala Tyr Leu Lys Lys Arg Cys Glu
            210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
            245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
            275                 280                 285

Lys Val Tyr Ala Glu Glu Ile Ala Gln Ala Trp Glu Ser Gly Glu Gly
            290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
            325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
            355                 360                 365

Pro Asn Lys Pro Asp Glu Arg Glu Leu Ala Arg Arg Gly Gly Tyr
            370                 375                 380

Ala Gly Gly Tyr Val Lys Glu Pro Glu Arg Gly Leu Trp Asp Asn Ile
385                 390                 395                 400

Val Tyr Leu Asp Phe Arg Ser His Val Asp Ser Ile Ile Thr His
            405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
            435                 440                 445

Ile Pro Ser Leu Leu Gly Asp Leu Leu Glu Glu Arg Gln Lys Ile Lys
            450                 455                 460

Arg Lys Met Lys Ala Thr Val Asp Pro Leu Glu Lys Lys Leu Leu Asp
465                 470                 475                 480

Tyr Arg Gln Arg Leu Ile Lys Ile Leu Ala Asn Ser Phe Tyr Gly Tyr
            485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
            515                 520                 525

Glu Glu Lys Phe Gly Phe Lys Val Leu Tyr Ala Asp Thr Asp Gly Leu
            530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
            565                 570                 575

```
Leu Glu Tyr Glu Gly Phe Tyr Val Arg Gly Phe Val Thr Lys Lys
            580                 585                 590

Lys Tyr Ala Val Ile Asp Glu Glu Gly Lys Ile Thr Thr Arg Gly Leu
            595                 600                 605

Glu Ile Val Arg Arg Asp Trp Ser Glu Ile Ala Lys Glu Thr Gln Ala
            610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Lys Arg Leu Ala Ala
            675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
            755                 760                 765

Leu Lys Val Lys Gly Lys Lys
770                 775

<210> SEQ ID NO 15
<211> LENGTH: 775
<212> TYPE: PRT
<213> ORGANISM: Thermococcus sp.

<400> SEQUENCE: 15

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
        50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Thr Met Leu Ala Phe Ala Ile Ala Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175
```

```
Asp Leu Pro Tyr Val Asp Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Met Val Asp Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Arg Lys Met Lys Ala Thr Val Asp Pro Leu Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590
```

```
Lys Tyr Ala Val Ile Asp Glu Glu Gly Lys Ile Thr Thr Arg Gly Leu
                595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
                660                 665                 670

Tyr Lys Ala Thr Gly Pro His Val Ala Val Ala Lys Arg Leu Ala Ala
                675                 680                 685

Arg Gly Val Lys Ile Arg Pro Gly Thr Val Ile Ser Tyr Ile Val Leu
                690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
                740                 745                 750

Glu Asp Leu Arg Tyr Gln Lys Thr Lys Gln Val Gly Leu Gly Ala Trp
                755                 760                 765

Leu Lys Val Lys Gly Lys Lys
                770                 775

<210> SEQ ID NO 16
<211> LENGTH: 775
<212> TYPE: PRT
<213> ORGANISM: Thermococcus sp.

<400> SEQUENCE: 16

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
                100                 105                 110

Asp Ile Pro Phe Ala Lys Arg Tyr Leu Ile Asp Lys Gly Leu Ile Pro
            115                 120                 125

Met Glu Gly Asp Glu Glu Leu Thr Met Leu Ala Phe Ala Ile Ala Thr
130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
                180                 185                 190
```

```
Arg Phe Leu Arg Val Val Arg Glu Lys Asp Pro Asp Val Leu Ile Thr
            195                 200                 205

Tyr Asn Gly Asp Asn Phe Asp Phe Ala Tyr Leu Lys Lys Arg Cys Glu
        210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
        370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Thr Val Asp Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
        450                 455                 460

Arg Lys Met Lys Ala Thr Val Asp Pro Leu Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
        530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605
```

-continued

Glu Ile Val Arg Arg Asp Trp Ser Glu Ile Ala Lys Glu Thr Gln Ala
610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
        645                 650                 655

Pro Glu Lys Leu Val Ile His Glu Gln Ile Thr Arg Asp Leu Arg Asp
        660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
        725                 730                 735

Val Leu Pro Ala Val Glu Arg Ile Leu Lys Ala Phe Gly Tyr Arg Lys
        740                 745                 750

Glu Asp Leu Arg Tyr Gln Lys Thr Lys Gln Val Gly Leu Gly Ala Trp
        755                 760                 765

Leu Lys Val Lys Gly Lys Lys
770                 775

<210> SEQ ID NO 17
<211> LENGTH: 775
<212> TYPE: PRT
<213> ORGANISM: Thermococcus sp.

<400> SEQUENCE: 17

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Thr Met Leu Ala Phe Ala Ile Ala Thr
130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

-continued

```
Tyr Asn Gly Asp Asn Phe Asp Phe Ala Tyr Leu Lys Lys Arg Cys Glu
        210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
                260                 265                 270

Tyr Thr Leu Glu Ala Val Tyr Glu Ala Val Phe Gly Lys Pro Lys Glu
            275                 280                 285

Lys Val Tyr Ala Glu Glu Ile Ala Gln Ala Trp Glu Ser Gly Glu Gly
290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
                340                 345                 350

Val Glu Trp Phe Leu Leu Arg Lys Ala Tyr Lys Arg Asn Glu Leu Ala
            355                 360                 365

Pro Asn Lys Pro Asp Glu Arg Glu Leu Ala Arg Arg Arg Gly Gly Tyr
        370                 375                 380

Ala Gly Gly Tyr Val Lys Glu Pro Glu Arg Gly Leu Trp Asp Asn Ile
385                 390                 395                 400

Val Tyr Leu Asp Phe Arg Ser His Thr Gln Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
            435                 440                 445

Ile Pro Ser Leu Leu Gly Asp Leu Leu Glu Glu Arg Gln Lys Ile Lys
        450                 455                 460

Arg Lys Met Lys Ala Thr Val Asp Pro Leu Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
            515                 520                 525

Glu Glu Lys Phe Gly Phe Lys Val Leu Tyr Ala Asp Thr Asp Gly Leu
        530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
            595                 600                 605

Glu Ile Val Arg Arg Asp Trp Ser Glu Ile Ala Lys Glu Thr Gln Ala
        610                 615                 620
```

-continued

```
Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
            645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
            725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
            755                 760                 765

Leu Lys Val Lys Gly Lys Lys
            770                 775

<210> SEQ ID NO 18
<211> LENGTH: 775
<212> TYPE: PRT
<213> ORGANISM: Thermococcus sp.

<400> SEQUENCE: 18

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
            115                 120                 125

Met Glu Gly Asp Glu Glu Leu Thr Met Leu Ala Phe Ala Ile Ala Thr
130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
            195                 200                 205

Tyr Asn Gly Asp Asn Phe Asp Phe Ala Tyr Leu Lys Lys Arg Cys Glu
210                 215                 220
```

-continued

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
            245                 250                 255

His Phe Asp Leu Tyr Pro Val Ile Arg Arg Thr Ile Asn Leu Pro Thr
        260                 265                 270

Tyr Thr Leu Glu Ala Val Tyr Glu Ala Val Phe Gly Lys Pro Lys Glu
    275                 280                 285

Lys Val Tyr Ala Glu Glu Ile Ala Gln Ala Trp Glu Ser Gly Glu Gly
290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Met Thr Gln Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Arg Lys Met Lys Ala Thr Val Asp Pro Leu Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

```
Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
            690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
            755                 760                 765

Leu Lys Val Lys Gly Lys Lys
            770                 775

<210> SEQ ID NO 19
<211> LENGTH: 775
<212> TYPE: PRT
<213> ORGANISM: Thermococcus sp.

<400> SEQUENCE: 19

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
            115                 120                 125

Met Glu Gly Asp Glu Glu Leu Thr Met Leu Ala Phe Ala Ile Ala Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
            195                 200                 205

Tyr Asn Gly Asp Asn Phe Asp Phe Ala Tyr Leu Lys Lys Arg Cys Glu
    210                 215                 220

Glu Leu Gly Ile Lys Phe Thr Leu Gly Arg Asp Gly Ser Glu Pro Lys
225                 230                 235                 240
```

```
Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
                260                 265                 270

Tyr Thr Leu Glu Ala Val Tyr Glu Ala Val Phe Gly Lys Pro Lys Glu
                275                 280                 285

Lys Val Tyr Ala Glu Glu Ile Ala Gln Ala Trp Glu Ser Gly Glu Gly
                290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
                340                 345                 350

Val Glu Trp Phe Leu Leu Arg Lys Ala Tyr Lys Arg Asn Glu Leu Ala
                355                 360                 365

Pro Asn Lys Pro Asp Glu Arg Glu Leu Ala Arg Arg Arg Gly Gly Tyr
                370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Thr Thr Gln Ser Ile Ile Thr His
                405                 410                 415

Asn Val Ser Pro Asp Thr Leu Asn Arg Glu Gly Cys Lys Glu Tyr Asp
                420                 425                 430

Val Ala Pro Glu Val Gly His Lys Phe Cys Lys Asp Phe Pro Gly Phe
                435                 440                 445

Ile Pro Ser Leu Leu Gly Asp Leu Leu Glu Glu Arg Gln Lys Ile Lys
                450                 455                 460

Arg Lys Met Lys Ala Thr Val Asp Pro Leu Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
                500                 505                 510

Val Thr Ala Trp Gly Arg Glu Tyr Ile Glu Met Val Ile Arg Glu Leu
                515                 520                 525

Glu Glu Lys Phe Gly Phe Lys Val Leu Tyr Ala Asp Thr Asp Gly Leu
                530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
                580                 585                 590

Lys Tyr Ala Val Ile Asp Glu Glu Gly Lys Ile Thr Thr Arg Gly Leu
                595                 600                 605

Glu Ile Val Arg Arg Asp Trp Ser Glu Ile Ala Lys Glu Thr Gln Ala
                610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655
```

-continued

```
Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Val Lys Gly Lys Lys
    770                 775

<210> SEQ ID NO 20
<211> LENGTH: 775
<212> TYPE: PRT
<213> ORGANISM: Thermococcus sp.

<400> SEQUENCE: 20

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Thr Met Leu Ala Phe Ala Ile Ala Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255
```

```
His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Thr Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser His Thr Asn Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Arg Lys Met Lys Ala Thr Val Asp Pro Leu Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670
```

```
Tyr Lys Ala Thr Gly Pro His Val Ala Val Ala Lys Arg Leu Ala Ala
    675             680             685

Arg Gly Val Lys Ile Arg Pro Gly Thr Val Ile Ser Tyr Ile Val Leu
    690             695             700

Lys Gly Ser Gly Arg Ile Gly Asp Arg Ala Ile Pro Ala Asp Glu Phe
705             710             715             720

Asp Pro Thr Lys His Arg Tyr Asp Ala Glu Tyr Tyr Ile Glu Asn Gln
            725             730             735

Val Leu Pro Ala Val Glu Arg Ile Leu Lys Ala Phe Gly Tyr Arg Lys
            740             745             750

Glu Asp Leu Arg Tyr Gln Lys Thr Lys Gln Val Gly Leu Gly Ala Trp
        755             760             765

Leu Lys Val Lys Gly Lys Lys
    770             775
```

POLYMERASE ENZYME FROM 9°N

CROSS-REFERENCE TO RELATED APPLICATIONS

This application is a continuation application of U.S. patent application Ser. No. 16/485,279, filed Aug. 12, 2019, which is a U.S. National Phase Application of International Application No. PCT/US2018/018004, filed Feb. 13, 2018, which claims the benefit of and priority to U.S. Provisional Patent Application No. 62/458,404, filed on Feb. 13, 2017, and European Patent Application No. 17160392.1, filed Mar. 10, 2017. The content of these earlier filed applications is hereby incorporated herein by reference in their entirety.

SEQUENCE LISTING

The present application contains a sequence listing that was submitted in ASCII format via EFS-Web concurrent with the filing of the application, containing the file name "37578.0053U3_Sequence_Listing," created on Jun. 17, 2021, and having a size of 135,168 bytes, and is hereby incorporated by reference in its entirety pursuant to 37 C.F.R. § 1.52(e)(5).

FIELD OF THE INVENTION

The present invention is in the field of molecular biology, in particular in the field of enzymes and more particular in the field of polymerases. It is also in the field of nucleic acid sequencing.

BACKGROUND

The invention relates to polymerase enzymes, in particular modified DNA polymerases which show improved incorporation of modified nucleotides compared to a control polymerase. Also included in the present invention are methods of using the modified polymerases for DNA sequencing, in particular next generation sequencing.

Three main super families of DNA polymerase exist, based upon their amino acid similarity to E. coli DNA polymerases I, II and III They are called family A, B and C polymerases respectively. Whilst crystallographic analysis of Family A and B polymerases reveals a common structural core for the nucleotide binding site, sequence motifs that are well conserved within families are only weakly conserved between families, and there are significant differences in the way these polymerases discriminate between nucleotide analogues. Early experiments with DNA polymerases revealed difficulties incorporating modified nucleotides such as dideoxynucleotides (ddNTPs). There are, therefore, several examples in which DNA polymerases have been modified to increase the rates of incorporation of nucleotide analogues. The majority of these have focused on variants of Family A polymerases with the aim of increasing the incorporation of dideoxynucleotide chain terminators. For example, Tabor, S. and Richardson, C. C. ((1995) Proc. Natl. Acad. Sci (USA) 92:6339) describe the replacement of phenylalanine 667 with tyrosine in T. aquaticus DNA polymerase and the effects this has on discrimination of dideoxynucleotides by the DNA polymerase.

In order to increase the efficiency of incorporation of modified nucleotides, DNA polymerases have been utilised or engineered such that they lack 3'-5' exonuclease activity (designated exo-). The exo-variant of 9° N polymerase is described by Perler et al., 1998 U.S. Pat. No. 5,756,334 and by Southworth et al., 1996 Proc. Natl Acad. Sci USA 93:5281.

Gardner A. F. and Jack W. E. (Determinants of nucleotide sugar recognition in an archaeon DNA polymerase Nucl. Acids Res. 27:2545, 1999) describe mutations in Vent DNA polymerase that enhance the incorporation of ribo-, 2' and 3'deoxyribo- and 2'-3'-dideoxy-ribonucleotides. The two individual mutations in Vent polymerase, Y412V and A488L, enhanced the relative activity of the enzyme with the nucleotide ATP. In addition, other substitutions at Y412 and A488 also increased ribonucleotide incorporation, though to a lesser degree. It was concluded that the bulk of the amino acid side chain at residue 412 acts as a "steric gate" to block access of the 2'-hydroxyl of the ribonucleotide sugar to the binding site. However, the rate enhancement with cordycepin (3'deoxy adenosine triphosphate) was only 2-fold, suggesting that the Y412V polymerase variant was also sensitive to the loss of the 3' sugar hydroxyl. For residue A488, the change in activity is less easily rationalized. A488 is predicted to point away from the nucleotide binding site; here the enhancement in activity was explained through a change to the activation energy required for the enzymatic reaction. These mutations in Vent correspond to Y409 and A485 in 9° N polymerase.

The universality of the A488L mutation has been confirmed by homologous mutations in the following hyperthermophilic polymerases:

A486Y variant of Pfu DNA polymerase (Evans et al., 2000. Nucl. Acids. Res. 28:1059). A series of random mutations was introduced into the polymerase gene and variants were identified that had improved incorporation of ddNTPs. The A486Y mutation improved the ratio of ddNTP/dNTP in sequencing ladders by 150-fold compared to wild type. However, mutation of Y410 to A or F produced a variant that resulted in an inferior sequencing ladder compared to the wild type enzyme. For further information, reference is made to International Publication No. WO 01/38546.

A485L variant of 9° N DNA polymerase (Gardner and Jack, 2002. Nucl. Acids. Res. 30:605). This study demonstrated that the mutation of Alanine to Leucine at amino acid 485 enhanced the incorporation of nucleotide analogues that lack a 3' sugar hydroxyl moiety (acyNTPs and dideoxy NTPs).

A485T variant of Tsp JDF-3 DNA polymerase (Arezi et al., 2002. J. Mol. Biol. 322:719). In this paper, random mutations were introduced into the JDF-3 polymerase from which variants were identified that had enhanced incorporation of ddNTPs. Individually, two mutations, A485T and P410L, improved ddNTP uptake compared to the wild type enzyme. In combination, these mutations had an additive effect and improved ddNTP incorporation by 250-fold. This paper demonstrates that the simultaneous mutation of two regions of a DNA polymerase can have additive effects on nucleotide analogue incorporation. In addition, this report demonstrates that P410, which lies adjacent to Y409 described above, also plays a role in the discrimination of nucleotide sugar analogues.

WO 01/23411 describes the use of the A488L variant of Vent in the incorporation of dideoxynucleotides and acyclonucleotides into DNA. The application also covers methods of sequencing that employ these nucleotide analogues and variants of 9° N DNA polymerase that are mutated at residue 485.

WO 2005/024010 A1 also relates to the modification of the motif A region and to the 9° N DNA polymerase. EP 1

664 287 B1 also relates to various altered family B type archeal polymerase enzymes which is capable of improved incorporation of nucleotides which have been modified at the 3' sugar hydroxyl such that the substituent is larger in size than the naturally occurring 3' hydroxyl group, compared to a control family B type archeal polymerase enzyme.

Yet, the modifications today still do not show sufficiently high incorporation rates of modified nucleotides (3'OH substituted analogs or having both substitutions on 3'-OH and carrying labels at the base). It would therefore be beneficial in order to improve sequencing performance to have enzymes that have such high incorporation rates of variety of modified nucleotides. One additional feature that is desirable is the tolerance for base modifications. For example, labels can be attached to the base or the 3'-OH via cleavable or non-cleavable linkers. In case of cleavable linkers attached to the base, there is usually a residual spacer arm left after the cleavage. This residual modification may interfere with incorporation of subsequent nucleotides by polymerase. Therefore, it is highly desirable to have polymerases for carrying out sequencing by synthesis process (SBS) that are tolerable of these scars.

SUMMARY OF THE INVENTION

In order to improve the efficiency of certain DNA sequencing methods, the inventors have analyzed whether such other DNA polymerases could be modified to produce improved rates of incorporation of such 3' substituted nucleotide analogues. Although some research had been done in this field, surprisingly improved enzymes were found.

The invention relates to a polymerase enzyme according to SEQ ID NO. 1 or any polymerase that shares at least 70% amino acid sequence identity thereto, comprising the following mutation(s):
  i. at position 408 of SEQ ID NO. 2 a mutation selected from:
    1. (H-histidine) (L408H),
    2. (M-methionine) (L408M),
    3. (T-threonine) (L408T),
    4. (G-glycine) (L408M),
    5. (N-asparagine) (L408N),
  ii. at position 409 of SEQ ID NO. 2 a mutation selected from:
    1. (T-threonine) (Y409T),
    2. (V-valine) (Y409V),
  iii. at position 410 of SEQ ID NO. 2 a mutation selected from:
    1. (C-cysteine) (P410C),
    2. (N-asparagine) (P410N),
    3. (D-aspartic acid) (P410D),
    4. (Q-glutamine) (P410Q),
  wherein the enzyme has little or no 3'-5' exonuclease activity.

In one embodiment polymerases also carry modifications/substitutions at position equivalent to 485 of SEQ ID NO. 1. Particularly preferred substitution is A→L. Substitutions at this position exhibit synergy with substitutions at positions 408/409/410 of SEQ ID NO. 1.

Preferably, the enzyme is from 9° N.

The invention also relates to the use of a modified polymerase in DNA sequencing and a kit comprising such an enzyme.

Herein, "incorporation" means joining of the modified nucleotide to the free 3' hydroxyl group of a second nucleotide via formation of a phosphodiester linkage with the 5' phosphate group of the modified nucleotide. The second nucleotide to which the modified nucleotide is joined will typically occur at the 3' end of a polynucleotide chain.

Herein, "modified nucleotides" and "nucleotide analogues" when used in the context of this invention refer to nucleotides which have been modified at the 3' sugar hydroxyl such that the substituent is larger in size than the naturally occurring 3' hydroxyl group. In addition, these nucleotides may carry additional modifications, such as detectable labels attached to the base moiety. These terms may be used interchangeably.

Herein, the term "large 3' substituent(s)" refers to a substituent group at the 3' sugar hydroxyl which is larger in size than the naturally occurring 3' hydroxyl group.

Herein, "improved" incorporation is defined to include an increase in the efficiency and/or observed rate of incorporation of at least one modified nucleotide, compared to a control polymerase enzyme. However, the invention is not limited just to improvements in absolute rate of incorporation of the modified nucleotides. As shown below the polymerases also incorporate other modifications and so called dark nucleotides (non-labeled, terminating or reversibly terminating), hence, "improved incorporation" is to be interpreted accordingly as also encompassing improvements in any of these other properties, with or without an increase in the rate of incorporation. For example, tolerance for modifications on the bases could be the result of the improved properties as could be ability to incorporate modified nucleotides at a range of concentrations and temperatures. The "improvement" need not be constant over all cycles. Herein, "improvement" may be the ability to incorporate the modified nucleotides at low temperatures and/or over a wider temperature range than the control enzyme. Herein, "improvement" may be the ability to incorporate the modified nucleotides when using a lower concentration of the modified nucleotides as substrate or lower concentration of polymerase. Preferably the altered polymerase should exhibit detectable incorporation of the modified nucleotide when working at a substrate concentration in the nanomolar range.

Herein, "altered polymerase enzyme" means that the polymerase has at least one amino acid change compared to the control polymerase enzyme. In general, this change will comprise the substitution of at least one amino acid for another. In certain instances, these changes will be conservative changes, to maintain the overall charge distribution of the protein. However, the invention is not limited to only conservative substitutions. Non-conservative substitutions are also envisaged in the present invention. Moreover, it is within the contemplation of the present invention that the modification in the polymerase sequence may be a deletion or addition of one or more amino acids from or to the protein, provided that the polymerase has improved activity with respect to the incorporation of nucleotides modified at the 3' sugar hydroxyl such that the substituent is larger in size than the naturally occurring 3' hydroxyl group as compared to a control polymerase enzyme, such as the enzyme of SEQ TD NO. 1 (lacking exonuclease activity).

The control polymerase may comprise any one of the listed substitution mutations functionally equivalent to the amino acid sequence of the given base polymerase (or an exo-variant thereof). Thus, the control polymerase may be a mutant version of the listed base polymerase having one of the stated mutations or combinations of mutations, and preferably having amino acid sequence identical to that of the base polymerase (or an exo-variant thereof) other than at the mutations recited above. Alternatively, the control polymerase may be a homologous mutant version of a polymerase other than the stated base polymerase, which includes a functionally equivalent or homologous mutation (or combination of mutations) to those recited in relation to the amino acid sequence of the base polymerase. By way of illustration, the control polymerase could be a mutant version of the Pfu polymerase having one of the mutations or combinations of mutations listed as optional or preferable above and below relative to the Pfu amino acid sequence, or it could be the 9° N polymerase or a mutant thereof or a mutant version of another polymerase. It would however not comprise the S-G-S mutation claimed herein.

Alternatively, the control polymerase is the wildtype 9° Nord polymerase with the SEQ ID No: 1.

The invention also encompasses enzymes claimed herein, wherein the amino acid sequence has been altered in non-conserved regions or positions. One skilled in the art will understand that many amino acid positions may be altered without changing the enzyme activity.

As used herein, the term, "nucleotide" comprises a purine or pyrimidine base linked glycosidically to a sugar (ribose or deoxyribose), and one or more phosphate groups attached to the 5' position of the sugar. "Nucleosides", as used herein, comprise a purine or pyrimidine base linked glycosidically to a sugar (ribose or deoxyribose), but lack a phosphate group at the 5' position of the sugar. With respect to the method claims described herein, it is generally understood that a nucleoside (lacking a 5' phosphate group) cannot be incorporated by a polymerase. Synthetic and naturally occurring nucleotides, prior to their modification at the 3' sugar hydroxyl, are included within the definition. Labeling of the bases can occur via naturally occurring groups (such as exocyclic amines for adenosine or guanosine) or via modifications, such as 5- and 7-deaza analogs. One preferred embodiment is attachment via 5-(pyrimidines) and 7-deaza (purines) propynyl group, more preferably propargylamine or propargylhydroxy group. Another preferred attachment is via hydroxymethyl groups as disclosed in U.S. Pat. No. 9,322,050.

Herein, and throughout the specification mutations within the amino acid sequence of a polymerase are written in the following form: (i) single letter amino acid as found in wild type polymerase, (ii) position of the change in the amino acid sequence of the polymerase and (iii) single letter amino acid as found in the altered polymerase. So, mutation of a Tyrosine residue in the wild type polymerase to a Valine residue in the altered polymerase at position 409 of the amino acid sequence would be written as Y409V. This is standard procedure in molecular biology.

DETAILED DESCRIPTION OF THE INVENTION

The sheer increase in rates of incorporation of the modified analogues that have been achieved with polymerases of the invention is unexpected. The examples show that even existing polymerases with mutations do not exhibit these high incorporation rates.

The invention relates to a polymerase enzyme according to SEQ ID NO. 1 or any polymerase that shares at least 70% amino acid sequence identity thereto, comprising the following mutation(s):
  i. at position 408 of SEQ ID NO. 1 a mutation selected from:
    5. (H-histidine) (L408H),
    6. (M-methionine) (L408M),
    7. (T-threonine) (L408T),
    8. (G-glycine) (L408M),
    9. (N-asparagine) (L408N),
  ii. at position 409 of SEQ ID NO. 2 a mutation selected from:
    10. (T-threonine) (Y409T),
    11. (V-valine) (Y409V),
  iii. at position 410 of SEQ ID NO. 2 a mutation selected from:
    12. (C-cysteine) (P410C).
    13. (N-asparagine) (P410N),
    14. (D-aspartic acid) (P410D),
    15. (Q-glutamine) (P410Q),
  wherein the enzyme has little or no 3'-5' exonuclease activity.

Preferably, the enzyme claimed shares 75%, 80%, 85%, 90%, 95%, 98%, 99%, 99.5% or 100% sequence identity with the enzyme according to SEQ ID NO. 1. These percentages do not include the additionally claimed mutations.

The invention also relates to a nucleic acid encoding an enzyme according to SEQ ID NO. 2 to 6.

The altered polymerase will generally and preferably be an "isolated" or "purified" polypeptide. By "isolated polypeptide" a polypeptide that is essentially free from contaminating cellular components is meant, such as carbohydrates, lipids, nucleic acids or other proteinaceous impurities which may be associated with the polypeptide in nature. One may use a His-tag for purification, but other means may also be used. Preferably, at least the altered polymerase may be a "recombinant" polypeptide.

The altered polymerase according to the invention may be a family B type DNA polymerase, or a mutant or variant thereof. Family B DNA polymerases include numerous archaeal DNA polymerase, human DNA polymerase α and T4, RB69 and φ29 phage DNA polymerases. Family A polymerases include polymerases such as Taq, and T7 DNA polymerase. In one embodiment the polymerase is selected from any family B archaeal DNA polymerase, human DNA polymerase α or T4, RB69 and φ29 phage DNA polymerases.

Preferably, the polymerase is from an organism belonging to the family of Thermococcaceae, preferably from the genera of Pyrococcus. Such organisms include, Pyrococcus abyssi, Pyrococcus woesei, Pyrococcus yayanosii, Pyrococcus horikoshii, Pryococcus furiosus or, e.g. Pryococcus glycovorans or 9° N.

Ideally, the polymerase comprises all of the following mutations, L408S, Y409G and P410S and optionally additionally, comprises one or more of the following additional mutations (numbering for 9° N) or equivalent mutations in other polymerase families: D141A, E143A, A485L. Mutations at 141/143 positions are known to eliminate most of the exonuclease proofreading ability. Mutations at position 485 are known to enhance incorporation of non-native nucleotides (terminator mutations); see Gardner and Jack, 2002. Nucl. Acids Res. 30:605.

Preferably, the enzyme additionally comprises a mutation A485L (numbering in numbering for 9° N 485).

Preferred is a polymerase, wherein the enzyme shares 95%, preferably even 98% sequence identity (not counting the mutations) with SEQ ID NO. 2 and additionally has the following set of mutations, (i) L408S, Y409G, P410S and (ii) A485L.

Preferred is a polymerase, wherein the enzyme shares 95%, preferably even 98% sequence identity with SEQ ID NO. 2, 3, 4, 5 or, 6.

Preferably, the modified polymerase comprises a mutation corresponding to A485L in 9° N polymerase. This mutation corresponds to A488L in Vent and A486L in Pfu. Several other groups have published on this mutation. A486Y variant of Pfu DNA polymerase (Evans et al., 2000. Nucl. Acids. Res. 28:1059). A series of random mutations was introduced into the polymerase gene and variants were identified that had improved incorporation of ddNTPs. The A486Y mutation improved the ratio of ddNTP/dNTP in sequencing ladders by 150-fold compared to wild type. However, mutation of Y410 to A or F produced a variant that resulted in an inferior sequencing ladder compared to the wild type enzyme; see also WO 01/38546. A485L variant of 9° N DNA polymerase (Gardner and Jack, 2002. Nucl. Acids Res. 30:605). This study demonstrated that the mutation of Alanine to Leucine at amino acid 485 enhanced the incorporation of nucleotide analogues that lack a 3' sugar hydroxyl moiety (acyNTPs and dideoxy NTPs). A485T variant of Tsp JDF-3 DNA polymerase (Arezi et al., 2002. J. Mol. Biol. 322:719). In this paper, random mutations were introduced into the JDF-3 polymerase from which variants were identified that had enhanced incorporation of ddNTPs. WO 01/23411 describes the use of the A488L variant of Vent in the incorporation of dideoxynucleotides and acyclonucleotides into DNA. The application also covers methods of sequencing that employ these nucleotide analogues and variants of 9° N DNA polymerase that are mutated at residue 485.

The invention relates to a polymerase with the mutations shown herein which exhibits an increased rate of incorporation of nucleotides which have been modified at the 3' sugar hydroxyl such that the substituent is larger in size than the naturally occurring 3' hydroxyl group and ddNTPs, compared to the control polymerase being a normal unmodified enzyme.

Such nucleotides are disclosed in WO 2004/018497 A2. Here, a modified nucleotide molecule comprising a purine or pyrimidine base and a ribose or deoxyribose sugar moiety having a removable 3'-OH blocking group covalently attached thereto, such that the 3' carbon atom has attached a group of the structure: —O—Z is disclosed, wherein Z is any of —C(R')$_2$—N(R")$_2$'C(R')$_2$—N(H)R", and —C(R')$_2$—N$_3$, wherein each R" is or is part of a removable protecting group; each R' is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy or amido group, or a detectable label attached through a linking group; or (R')$_2$ represents an alkylidene group of formula =C(R''')$_2$ wherein each R''' may be the same or different and is selected from the group comprising hydrogen and halogen atoms and alkyl groups; and wherein said molecule may be reacted to yield an intermediate in which each R" is exchanged for H, which intermediate dissociates under aqueous conditions to afford a molecule with a free 3'OH.

The inventors have found that the claimed polymerase may be used in extension reactions and sequencing reactions very well when a novel nucleotide is used. Thus, the invention relates to a method of sequencing a nucleic acid wherein the claimed polymerase is used together with the following nucleotide.

In a preferred embodiment nucleotide has the following characteristics. The nucleotide comprises a nucleobase, a sugar, and at least one phosphate group at the 5' position, wherein said nucleobase comprising a detectable label attached via a cleavable oxymethylenedisulfide linker, said sugar comprising a 3'-0 capped by a cleavable protecting group comprising methylenedisulfide.

Ideally, the nucleobase is a non-natural nucleobase and is selected from the group comprising 7-deaza guanine, 7-deaza adenine, 2-amino,7-deaza adenine, and 2-amino adenine.

Ideally, the cleavable protecting group is of the formula —CH$_2$—SS—R, wherein R is selected from the group comprising alkyl and substituted alkyl groups.

Preferably, the nucleotide has this structure:

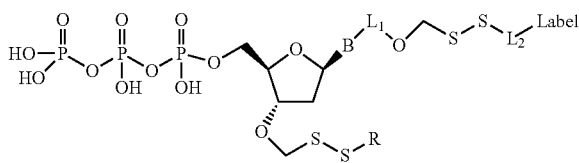

Here, B is a nucleobase, R is selected from the group comprising alkyl and substituted alkyl groups, and L1 and L2 are connecting groups. Preferably, $L_1$ and $L_2$ are independently selected from the group comprising —CO—, —CONH—, —NHCONH—, —O—, —S—, —ON, and —N=N—, alkyl, aryl, branched alkyl, branched aryl. Ideally $L_1$ and $L_2$ are the same.

The invention relates to a kit comprising a DNA polymerase as disclosed herein and claimed herein, and at least one nucleotide (e.g. a deoxynucleotide triphosphate) comprising a nucleobase, a sugar, and at least one phosphate group at the 5' position, wherein said sugar comprising a cleavable protecting group on the 3'-O, wherein said cleavable protecting group comprises methylenedisulfide, and wherein said nucleotide further comprises a detectable label attached via a cleavable oxymethylenedisulfide linker to the nucleobase of said nucleotide.

Claimed is also a reaction mixture comprising a nucleic acid template with a primer hybridized to said template, a DNA polymerase according to the invention and at least one nucleotide comprising a nucleobase, a sugar, and at least one phosphate group at the 5' position, wherein said sugar comprising a cleavable protecting group on the 3'-O, wherein said cleavable protecting group comprises methylenedisulfide, wherein said nucleotide further comprises a detectable label attached via a cleavable oxymethylenedisulfide linker to the nucleobase of said nucleotide.

Claimed is a method of performing a DNA synthesis reaction comprising the steps of a) providing a nucleic acid template with a primer hybridized to said template, the DNA polymerase according to the invention, at least one nucleotide comprising a nucleobase, a sugar, and at least one phosphate group at the 5' position, wherein said sugar comprising a cleavable protecting group on the 3'-O, wherein said cleavable protecting group comprises methylenedisulfide, wherein said nucleotide further comprises a detectable label attached via a cleavable oxymethylenedisulfide linker to the nucleobase of said nucleotide, and b) subjecting said reaction mixture to conditions which enable a DNA polymerase catalyzed primer extension reaction.

The invention also relates to a method for analyzing a DNA sequence comprising the steps of a) providing a nucleic acid template with a primer hybridized to said template forming a primer/template hybridization complex, b) adding DNA polymerase according to the invention, and a first nucleotide comprising a nucleobase, a sugar, and at least one phosphate group at the 5' position, wherein said sugar comprising a cleavable protecting group on the 3'-O, wherein said cleavable protecting group comprises methylenedisulfide, wherein said nucleotide further comprises a first detectable label attached via a cleavable oxymethylenedisulfide linker to the nucleobase of said nucleotide, c) subjecting said reaction mixture to conditions which enable a DNA polymerase catalyzed primer extension reaction so as to create a modified primer/template hybridization complex, and d) detecting a said first detectable label of said nucleotide in said modified primer/template hybridization complex. The blocking group may be repeatedly removed and novel nucleotides added. These methods are known to the person skilled in the art. Here, differently labeled, 3-O methylenedisulfide capped nucleotide compounds representing analogs of A, G, C and T or U are used in step b). Ideally, step e) is performed by exposing said modified primer/template hybridization complex to a reducing agent. This can be TCEP.

In another embodiment the labelled nucleotide that is used is as follows.

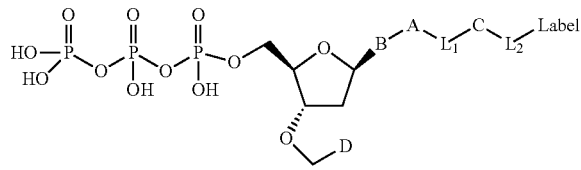

Here, D is selected from the group consisting of an azide, disulfide alkyl and disulfide substituted alkyl groups, B is a nucleobase, A is an attachment group, C is a cleavable site core, $L_1$ and $L_2$ are connecting groups, and Label is a label. Ideally, the nucleobase is selected from the group of 7-deaza guanine, 7-deaza adenine, 2-amino,7-deaza adenine, and 2-amino adenine.

$L_1$ is selected from the group consisting of —CONH$(CH_2)_x$—, —CO—O$(CH_2)_x$—, —CONH—$(OCH_2CH_2O)_x$—, CO—O$(CH_2CH_2O)_x$— and —CO$(CH_2)_x$— wherein x is 0-10. $L_2$ can be,

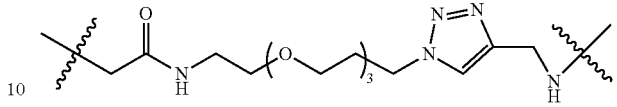

$L_2$ can be, —NH—, —$(CH_2)_x$—NH—, —C(Me)$_2$$(CH_2)_x$NH—, —CH(Me)$(CH_2)_x$NH—, —C(Me)$_2$$(CH_2)_x$CO—, —CH(Me)$(CH_2)_x$CO—, —$(CH_2)_x$OCONH$(CH_2)_y$O$(CH_2)_z$NH—, —$(CH_2)_x$CONH$(CH_2CH_2O)_y$$(CH_2)_z$NH—, and —CONH$(CH_2)_x$—, —CO$(CH_2)_x$— wherein x, y, and z are each independently selected from is 0-10.

Preferably the labeled nucleotide has the following structure:

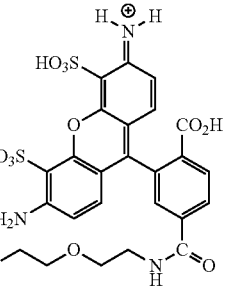
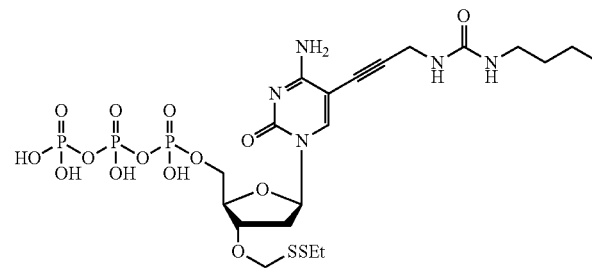

Preferably the labeled nucleotide has the following structure:

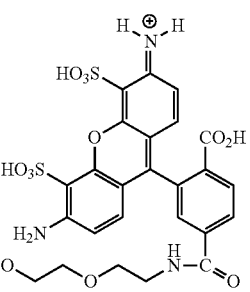
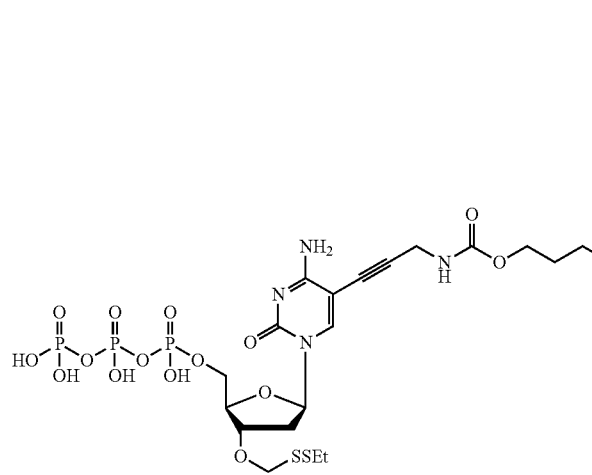

Preferably the labeled nucleotide has the following structure:
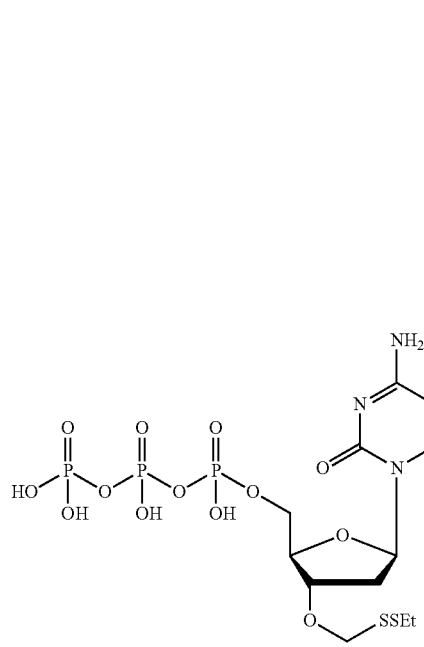
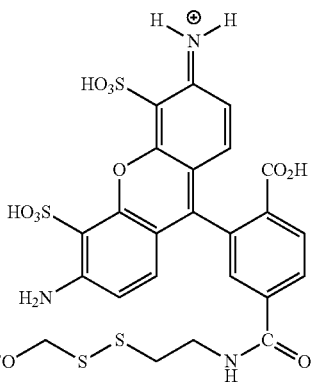
Preferably the labeled nucleotide has the following structure:
30
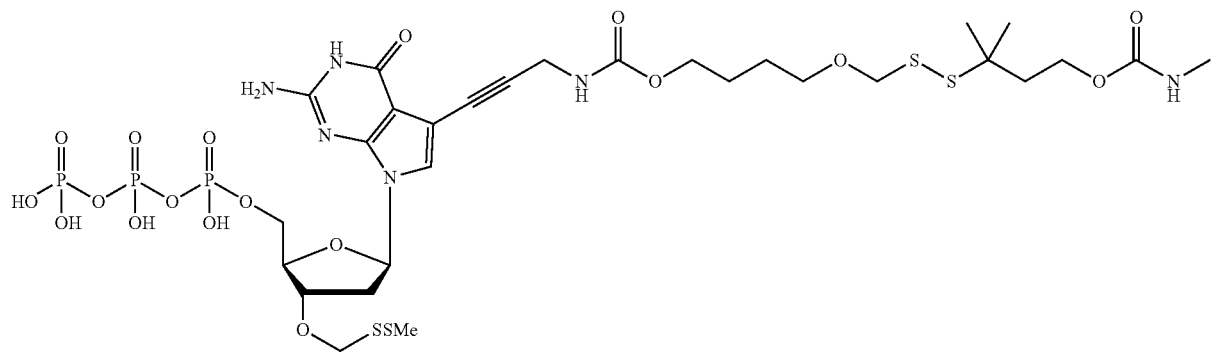
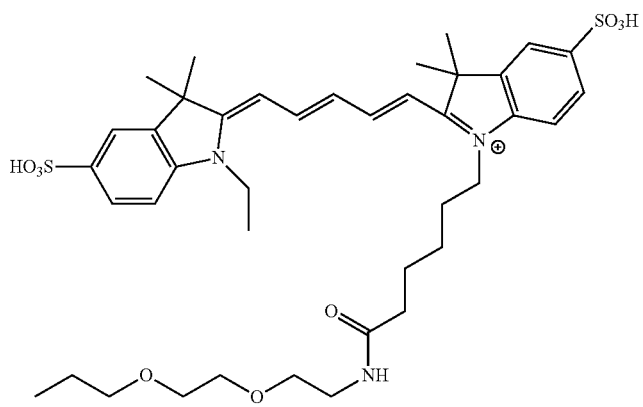

Preferably the labeled nucleotide has the following structure:
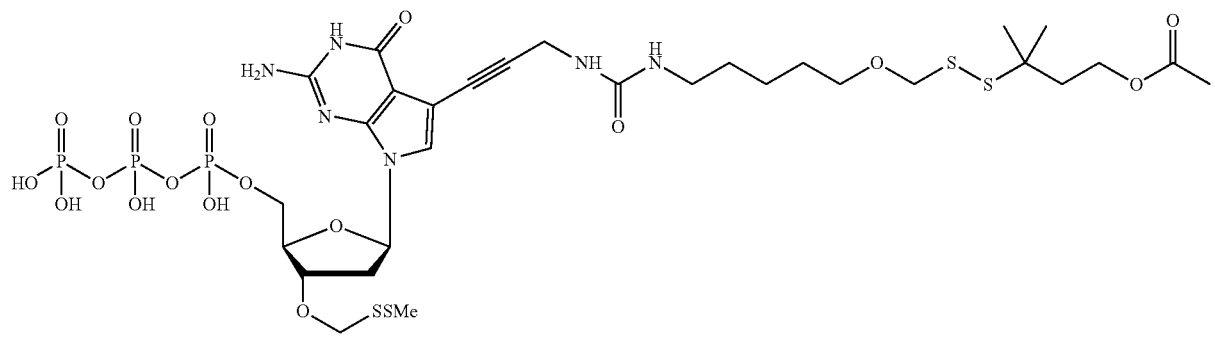
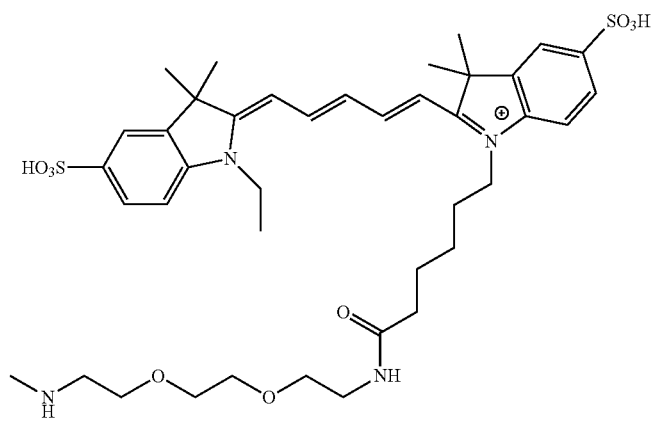
Preferably the labeled nucleotide has the following structure:
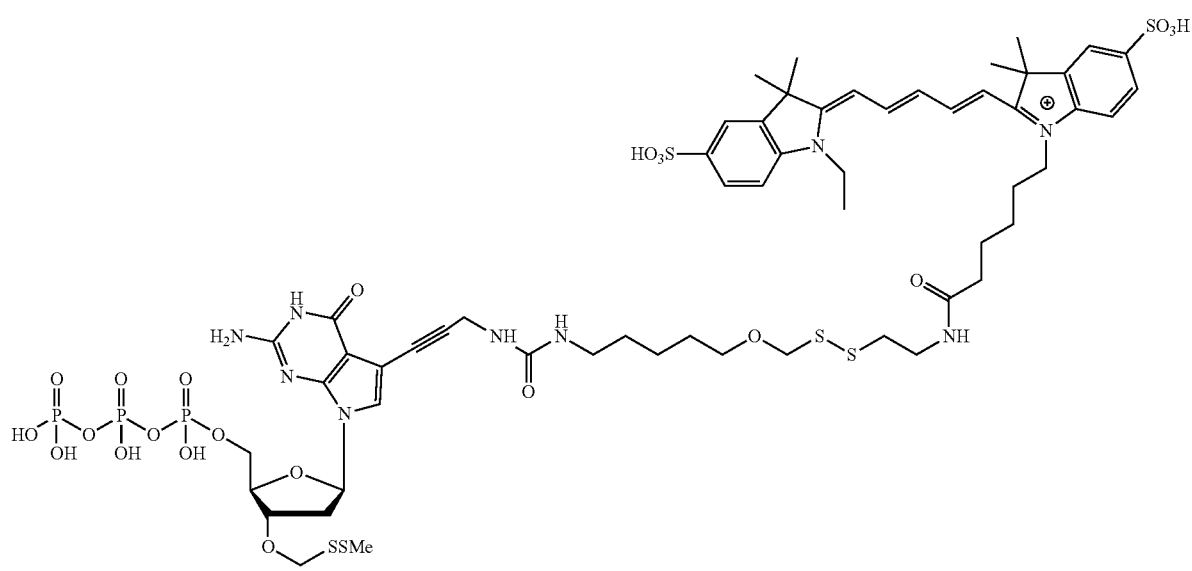

Preferably the labeled nucleotide has the following structure:
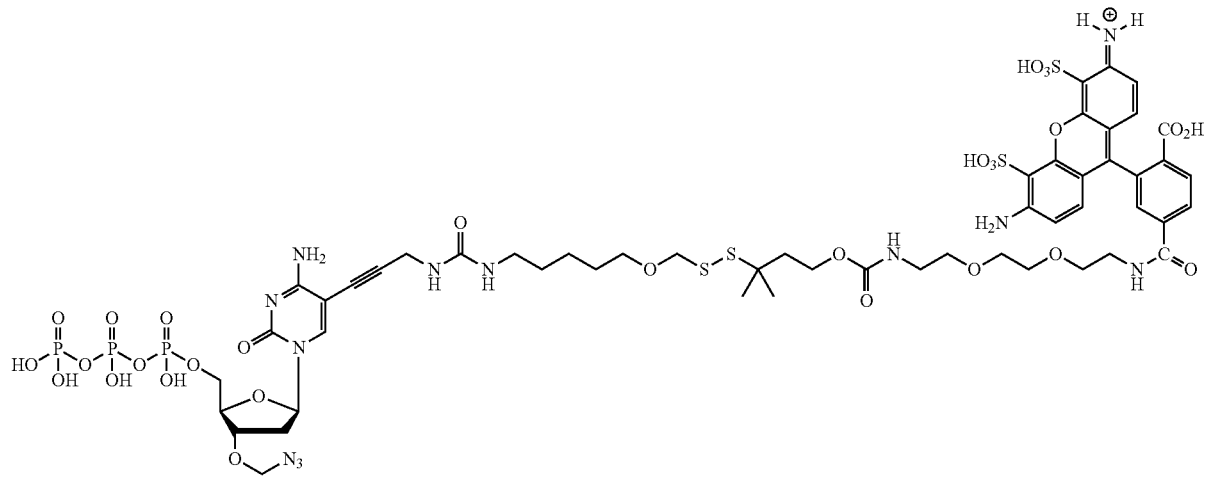 [SMILES: CC(C)(CCOC(=O)NCCOCCOCCNC(=O)c1ccc(C(=O)O)c(-c2c3ccc(=[NH2+])c(S(=O)(=O)O)c-3oc3c(S(=O)(=O)O)c(N)ccc23)c1)SSCOCCCCCNC(=O)NCC#Cc1cn([C@H]2C[C@@H](OCN=[N+]=[N-])[C@@H](COP(=O)(O)OP(=O)(O)OP(=O)(O)O)O2)c(=O)nc1N]
Preferably the labeled nucleotide has the following structure:
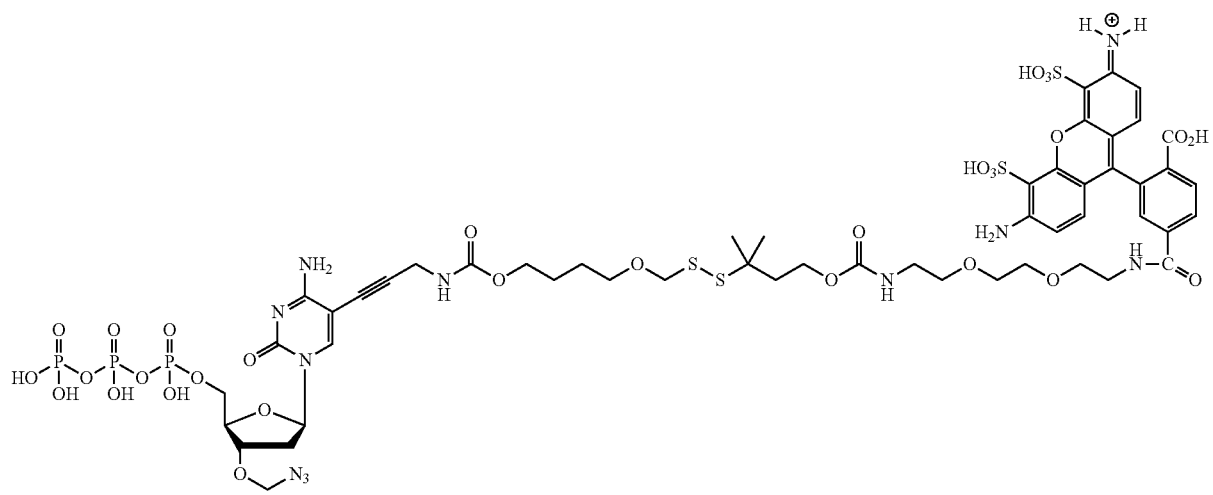 [SMILES: CC(C)(CCOC(=O)NCCOCCOCCNC(=O)c1ccc(C(=O)O)c(-c2c3ccc(=[NH2+])c(S(=O)(=O)O)c-3oc3c(S(=O)(=O)O)c(N)ccc23)c1)SSCOCCCCOC(=O)NCC#Cc1cn([C@H]2C[C@@H](OCN=[N+]=[N-])[C@@H](COP(=O)(O)OP(=O)(O)OP(=O)(O)O)O2)c(=O)nc1N]

Preferably the labeled nucleotide has the following structure:
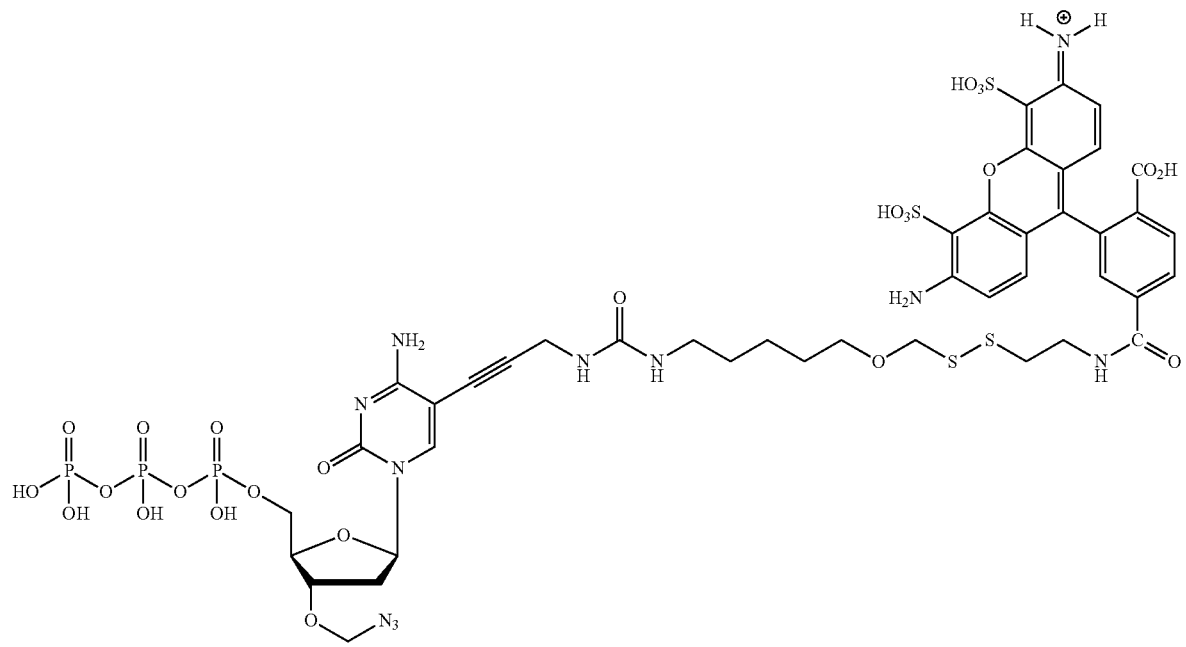 [SMILES: [N-]=[N+]=NCO[C@@H]1C[C@H](n2cc(C#CCNC(=O)NCCCCCOCSSCCNC(=O)c3ccc(C(=O)O)c(-c4c5ccc(=[NH2+])c(S(=O)(=O)O)c-5oc5c(S(=O)(=O)O)c(N)ccc45)c3)c(N)nc2=O)O[C@@H]1COP(=O)(O)OP(=O)(O)OP(=O)(O)O]
Preferably the labeled nucleotides have the following structures:
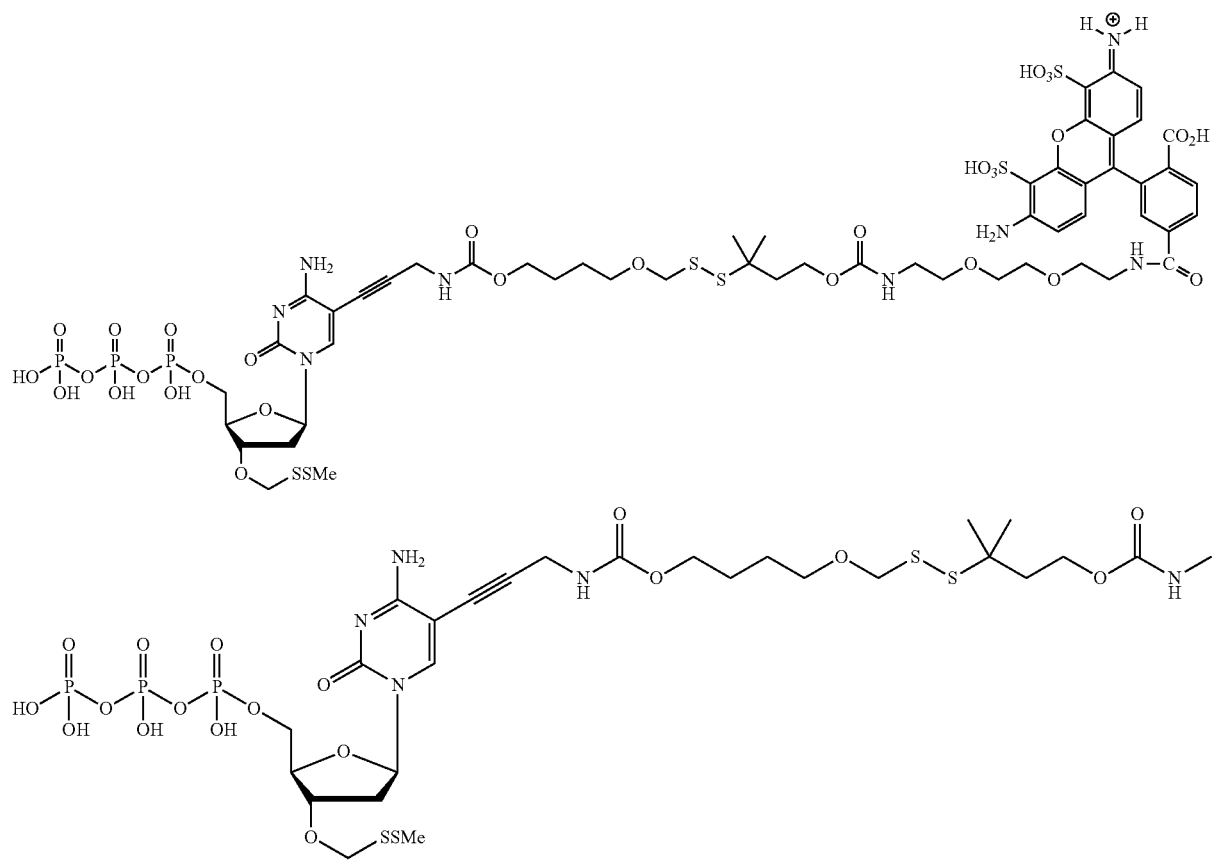

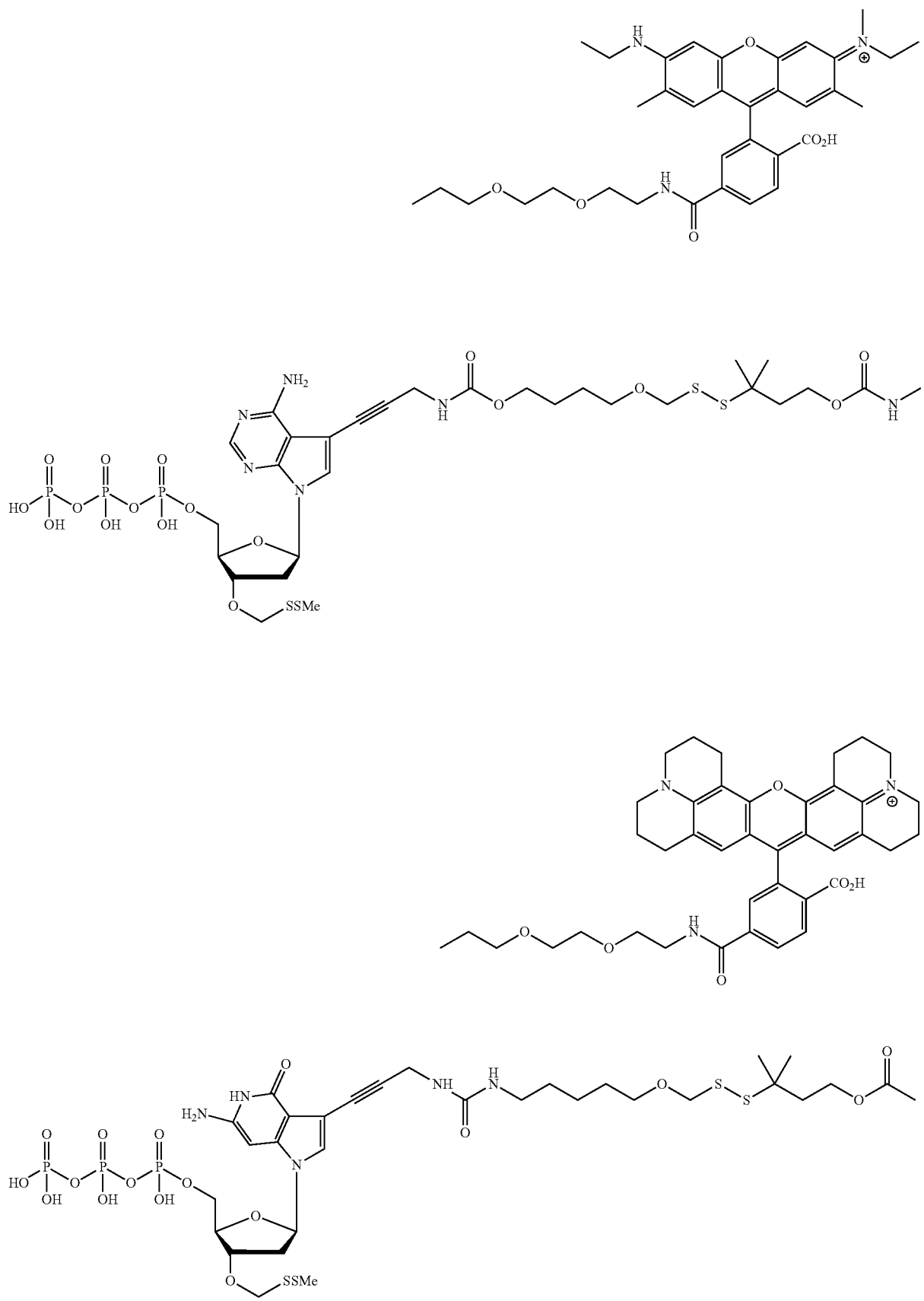

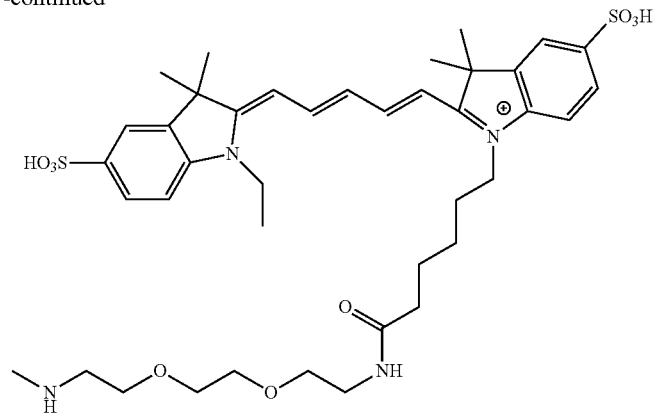

Preferably the non-labeled nucleotides have the following structures:

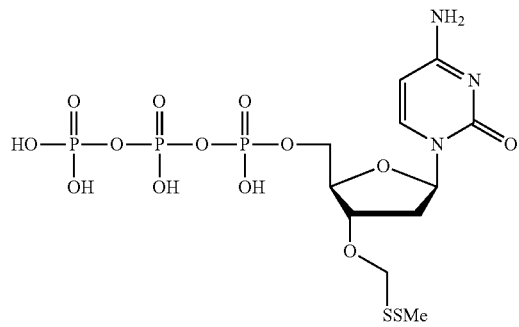

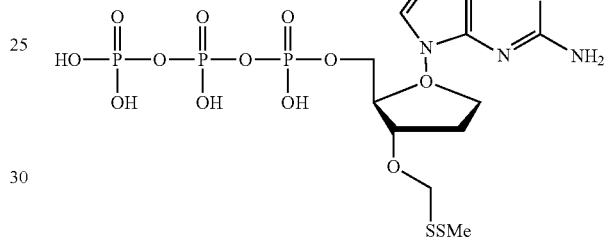

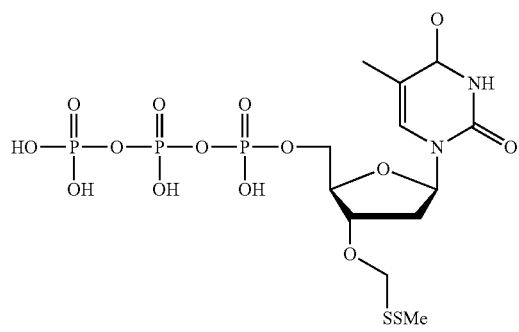

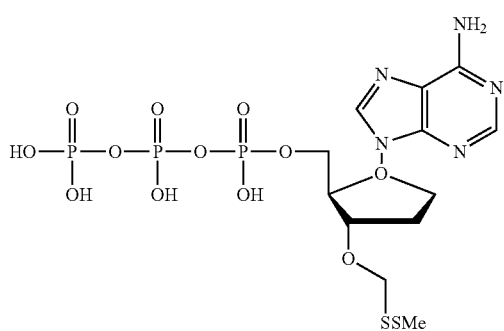

The invention also relates to a nucleic acid molecule encoding a polymerase according to the invention, as well as an expression vector comprising said nucleic acid molecule.

The invention also relates to a method for incorporating nucleotides which have been modified at the 3' sugar hydroxyl such that the substituent is larger in size than the naturally occurring 3' hydroxyl group into DNA comprising the following substances (i) a polymerase according to any one of the previous embodiments, (ii) template DNA, (iii) one or more nucleotides, which have been modified at the 3' sugar hydroxyl such that the substituent is larger in size than the naturally occurring 3' hydroxyl group.

The invention also relates to a method for incorporating nucleotides which have been modified at the 3' sugar hydroxyl such that the substituent is larger in size than the naturally occurring 3' hydroxyl group into DNA comprising the following substances (i) a polymerase according to any one of the previous embodiments, (ii) template DNA, (iii) one or more nucleotides, which have been modified at the 3' sugar hydroxyl such that the substituent is larger in size than the naturally occurring 3' hydroxyl group, wherein the blocking group comprises a disulfide preferably, methylene-disulfide.

The invention also relates to the use of a polymerase according to the invention in methods such as nucleic acid labeling, or sequencing. The polymerases of the present invention are useful in a variety of techniques requiring incorporation of a nucleotide into a polynucleotide, which include sequencing reactions, polynucleotide synthesis, nucleic acid amplification, nucleic acid hybridization assays, single nucleotide polymorphism studies, and other such techniques. All such uses and methods utilizing the modified polymerases of the invention are included within the scope of the present invention.

In sequencing the use of nucleotides bearing a 3' block allows successive nucleotides to be incorporated into a polynucleotide chain in a controlled manner. After each nucleotide addition the presence of the 3' block prevents incorporation of a further nucleotide into the chain. Once the nature of the incorporated nucleotide has been determined, the block may be removed, leaving a free 3' hydroxyl group for addition of the next nucleotide. Sequencing by synthesis of DNA ideally requires the controlled (i.e. one at a time) incorporation of the correct complementary nucleotide opposite the oligonucleotide being sequenced. This allows for accurate sequencing by adding nucleotides in multiple cycles as each nucleotide residue is sequenced one at a time, thus preventing an uncontrolled series of incorporations occurring. The incorporated nucleotide is read using an appropriate label attached thereto before removal of the label moiety and the subsequent next round of sequencing. In order to ensure only a single incorporation occurs, a structural modification ("blocking group") of the sequencing nucleotides is required to ensure a single nucleotide incorporation but which then prevents any further nucleotide incorporation into the polynucleotide chain. The blocking group must then be removable, under reaction conditions which do not interfere with the integrity of the DNA being sequenced. The sequencing cycle can then continue with the incorporation of the next blocked, labelled nucleotide. In order to be of practical use, the entire process should consist of high yielding, highly specific chemical and enzymatic steps to facilitate multiple cycles of sequencing. To be useful in DNA sequencing, a nucleotide, and more usually nucleotide triphosphates, generally require a 3 OH-blocking group so as to prevent the polymerase used to incorporate it into a polynucleotide chain from continuing to replicate once the base on the nucleotide is added. The DNA template for a sequencing reaction will typically comprise a double-stranded region having a free 3' hydroxyl group which serves as a primer or initiation point for the addition of further nucleotides in the sequencing reaction. The region of the DNA template to be sequenced will overhang this free 3' hydroxyl group on the complementary strand. The primer bearing the free 3' hydroxyl group may be added as a separate component (e.g. a short oligonucleotide) which hybridizes to a region of the template to be sequenced. Alternatively, the primer and the template strand to be sequenced may each form part of a partially self-complementary nucleic acid strand capable of forming an intramolecular duplex, such as for example a hairpin loop structure. Nucleotides are added successively to the free 3' hydroxyl group, resulting in synthesis of a polynucleotide chain in the 5' to 3' direction. After each nucleotide addition the nature of the base which has been added will be determined, thus providing sequence information for the DNA template.

Such DNA sequencing may be possible if the modified nucleotides can act as chain terminators. Once the modified nucleotide has been incorporated into the growing polynucleotide chain complementary to the region of the template being sequenced there is no free 3'-OH group available to direct further sequence extension and therefore the polymerase can not add further nucleotides. Once the nature of the base incorporated into the growing chain has been determined, the 3' block may be removed to allow addition of the next successive nucleotide. By ordering the products derived using these modified nucleotides it is possible to deduce the DNA sequence of the DNA template. Such reactions can be done in a single experiment if each of the modified nucleotides has attached a different label, known to correspond to the particular base, to facilitate discrimination between the bases added at each incorporation step. Alternatively, a separate reaction may be carried out containing each of the modified nucleotides separately.

In a preferred embodiment the modified nucleotides carry a label to facilitate their detection. Preferably this is a fluorescent label. Each nucleotide type may carry a different fluorescent label. However, the detectable label need not be a fluorescent label. Any label can be used which allows the detection of the incorporation of the nucleotide into the DNA sequence.

One method for detecting the fluorescently labelled nucleotides, suitable for use in the second and third aspects of the invention, comprises using laser light of a wavelength specific for the labelled nucleotides, or the use of other suitable sources of illumination.

In one embodiment the fluorescence from the label on the nucleotide may be detected by a CCD camera.

If the DNA templates are immobilised on a surface they may preferably be immobilised on a surface to form a high density array. Most preferably, and in accordance with the technology developed by the applicants for the present invention, the high density array comprises a single molecule array, wherein there is a single DNA molecule at each discrete site that is detectable on the array. Single-molecule arrays comprised of nucleic acid molecules that are individually resolvable by optical means and the use of such arrays in sequencing are described, for example, in WO 00/06770, the contents of which are incorporated herein by reference. Single molecule arrays comprised of individually resolvable nucleic acid molecules including a hairpin loop structure are described in WO 01/57248, the contents of which are also incorporated herein by reference. The polymerases of the invention are suitable for use in conjunction with single molecule arrays prepared according to the disclosures of WO 00/06770 of WO 01/57248. However, it is to be understood that the scope of the invention is not intended to be limited to the use of the polymerases in connection with single molecule arrays. Single molecule array-based sequencing methods may work by adding fluorescently labelled modified nucleotides and an altered polymerase to the single molecule array. Complementary nucleotides would base-pair to the first base of each nucleotide fragment and would be added to the primer in a reaction catalysed by the improved polymerase enzyme. Remaining free nucleotides would be removed. Then, laser light of a specific wavelength for each modified nucleotide would excite the appropriate label on the incorporated modified nucleotides, leading to the fluorescence of the label. This fluorescence could be detected by a suitable CCD camera that can scan the entire array to identify the incorporated modified nucleotides on each fragment. Thus millions of sites could potentially be detected in parallel. Fluorescence could then be removed. The identity of the incorporated modified nucleotide would reveal the identity of the base in the sample sequence to which it is paired. The cycle of incorporation, detection and identification would then be repeated approximately 25 times to determine the first 25 bases in each oligonucleotide fragment attached to the array, which is detectable. Thus, by simultaneously sequencing all molecules on the array, which are detectable, the first 25 bases for the hundreds of millions of oligonucleotide fragments attached in single copy to the array could be determined. Obviously the invention is not limited to sequencing 25 bases. Many more or less bases could be sequenced depending on the level of detail of sequence information required and the complexity of the array. Using a suitable bioinformatics program the generated sequences could be aligned and compared to specific reference sequences. This would allow determination of any number of known and unknown genetic variations such as single nucleotide polymorphisms (SNPs) for example. The utility of the altered polymerases of the invention is not limited to sequencing applications using single-molecule arrays. The polymerases may be used in conjunction with any type of array-based (and particularly any high density array-based) sequencing technology requiring the use of a polymerase to incorporate nucleotides into a polynucleotide chain, and in particular any array-based sequencing technology which relies on the incorporation of modified nucleotides having large 3' substituents (larger than natural hydroxyl group), such as 3' blocking groups. The polymerases of the invention may be used for nucleic acid sequencing on essentially any type of array formed by immobilisation of nucleic acid molecules on a solid support. In addition to single molecule arrays suitable arrays may include, for example, multi-polynucleotide or clustered arrays in which distinct regions on the array comprise multiple copies of one individual polynucleotide molecule or even multiple copies of a small-number of different polynucleotide molecules (e.g. multiple copies of two complementary nucleic acid strands). In particular, the polymerases of the invention may be utilised in the nucleic acid sequencing method described in WO 98/44152, the contents of which are incorporated herein by reference. This International application describes a method of parallel sequencing of multiple templates located at distinct locations on a solid support. The method relies on incorporation of labelled nucleotides into a polynucleotide chain. The polymerases of the invention may be used in the method described in International Application WO 00/18957, the contents of which are incorporated herein by reference. This application describes a method of solid-phase nucleic acid amplification and sequencing in which a large number of distinct nucleic acid molecules are arrayed and amplified simultaneously at high density via formation of nucleic acid colonies and the nucleic acid colonies are subsequently sequenced. The altered polymerases of the invention may be utilised in the sequencing step of this method. Multi-polynucleotide or clustered arrays of nucleic acid molecules may be produced using techniques generally known in the art. By way of example, WO 98/44151 and WO 00/18957 both describe methods of nucleic acid amplification which allow amplification products to be immobilised on a solid support in order to form arrays comprised of clusters or "colonies" of immobilised nucleic acid molecules. The contents of WO 98/44151 and WO 00/18957 relating to the preparation of clustered arrays and use of such arrays as templates for nucleic acid sequencing are incorporated herein by reference. The nucleic acid molecules present on the clustered arrays prepared according to these methods are suitable templates for sequencing using the polymerases of the invention. However, the invention is not intended to use of the polymerases in sequencing reactions carried out on clustered arrays prepared according to these specific methods. The polymerases of the invention may further be used in methods of fluorescent in situ sequencing, such as that described by Mitra et al. Analytical Biochemistry 320, 55-65, 2003 and Lee et al, Nature Protocols 10, 442-458 (2015).

Additionally, in another aspect, the invention provides a kit, comprising: (a) the polymerase according to the invention, and optionally, a plurality of different individual nucleotides of the invention and/or packaging materials therefor.

Several Experiments were carried out to show the increased rate of incorporation of nucleotides which have been modified compared to different wildtype polymerases and polymerases of the state of the art. Some of the results are shown in FIGS. 5, 6, 8 to 10 and 11. Further results with other wildtype polymerases and mutated polymerases from the state of the art also showed an increased rate of incorporation of nucleotides which have been modified as well as an enhanced specificity and sensitivity of the mutated polymerases according to the invention. The polymerases according to the invention show enhanced activity for incorporating bulky nucleotides also when compared to those disclosed in EP 1 664 287 B1.

FIGURE CAPTIONS

FIG. 5 shows the performance improvement for the preferred motif polymerase as measured by sequencing KPIs (error rate, false positives) and comparison with control polymerase (T9). One may observe a substantial decrease in false positives for Jpol 5 (SEQ ID NO. 2) and JPol 8 (SEQ ID NO. 3) relative to T9. These new enzymes have a reduced incorporation bias. A false positive can be defined as a variant that the GR calls. The gold standard is a quality score of higher than 15 and a coverage of higher than 200× as well as reduced rate of false positive variants clearly shown for JPol 5 and JPol 8.

Figure 6:
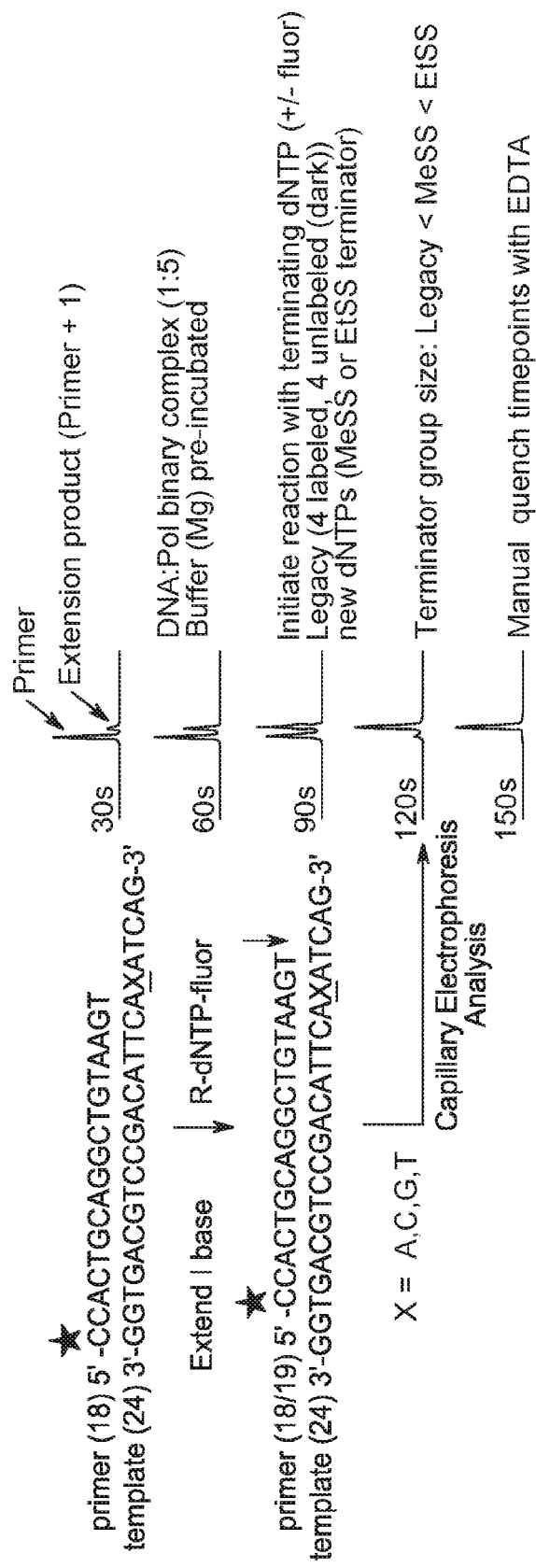

FIG. 6 shows the measurement of polymerase performance using extension in solution and capillary electrophoresis. The rate of single base terminating dNTP incorporation is measured. The extended fluorescent primer is detected by capillary electrophoresis (CE). The relative rate dNTP addition is determined by plots of fraction extended primer over time.

Figure 7:
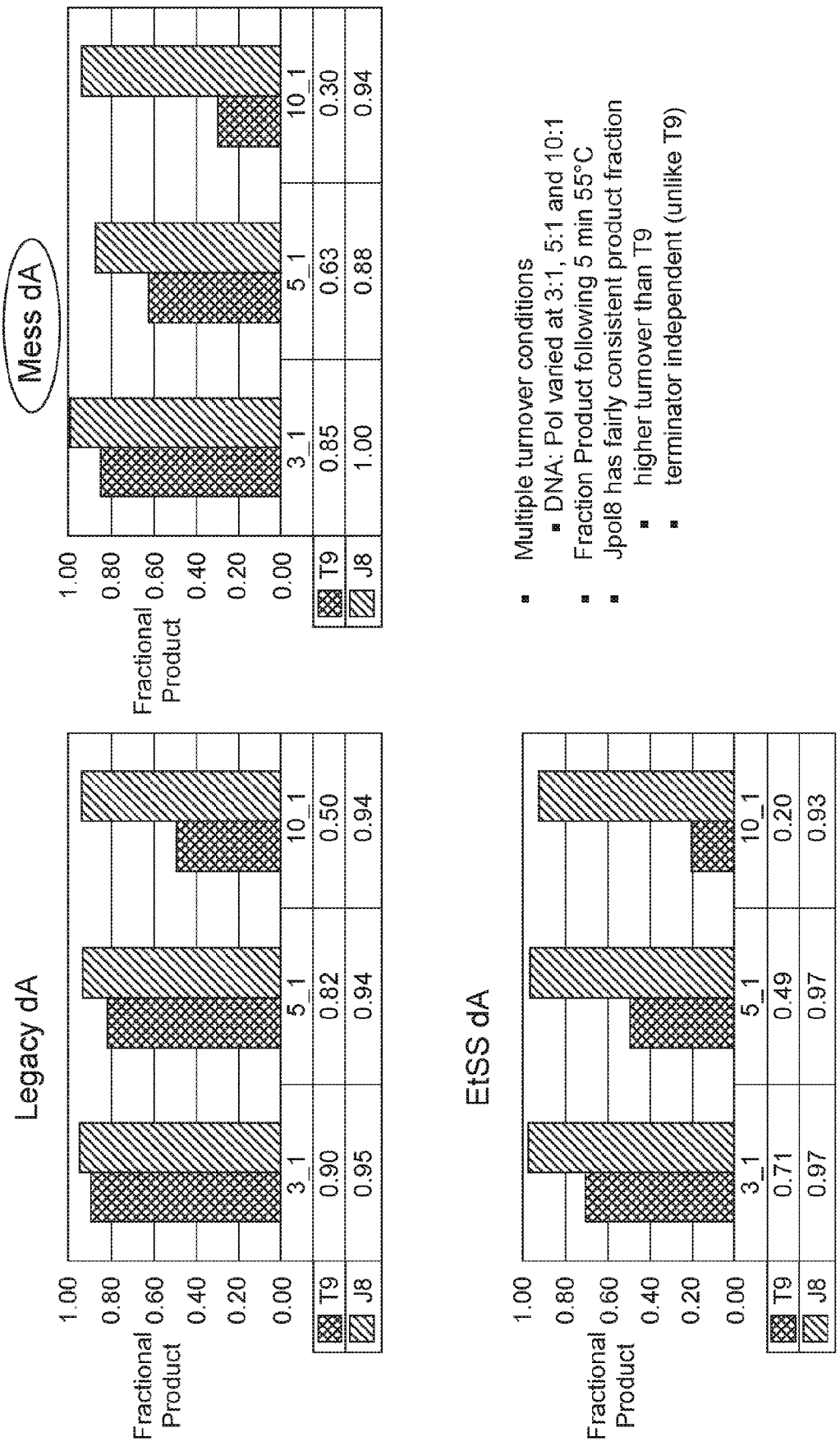

FIG. 7 shows a comparison of legacy (T9) and polymerase Jpol8 (SEQ ID NO. 3) using multiple turnover assay and 3 different classes of reversibly terminating nucleotides. The assay was done with multiple turnover conditions DNA:POL ratio was varied 3:1, 5:1 and 10:1. Under assay conditions for each polymerase molecule there are 3, 5 or 10 DNA template molecules which need to be extended. For the polymerase to be effective under these conditions it will need to bind to the primer/template duplex, incorporate the nucleotide analog and then dissociate and bind to another primer/template duplex molecule. JPol8 shows superior performance as indicated by higher degree of extended product fraction irrespective of the ratio and nature of reversibly terminating group on the 3'-OH of the nucleotide.

Figure 8:
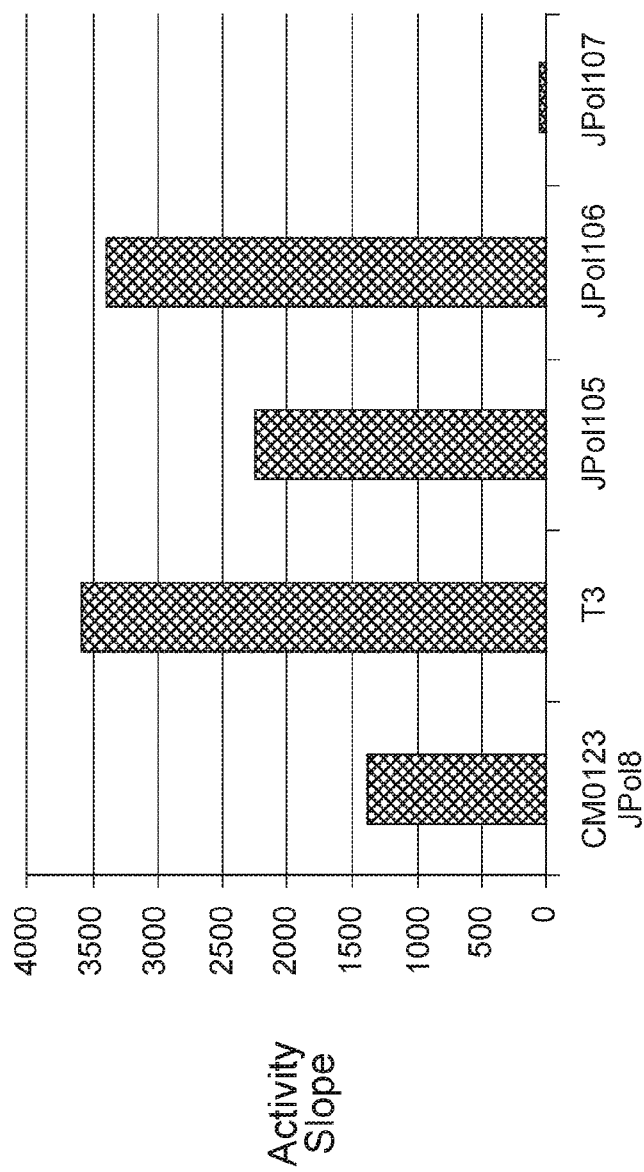

FIG. 8 shows an assay for polymerase activity with native nucleotides by Jpol 8 (SEQ ID NO. 3), JPol 105 (SEQ ID NO. 4), JPol 106 (SEQ ID NO. 5), and JPol107 (SEQ ID NO. 6). These assays are used to establish the enzyme produced is active and serves only to qualify the enzymes for further evaluations with nucleotide analogs (such as reversibly terminating ones). They rely on ability to polymerize DNA in the presence of native nucleotides and serves the purpose to establish specific activity for given polymerase preparation. The measurement uses intercalating dye/fluorescence and specific activity is proportional to the slope.

Figure 9:
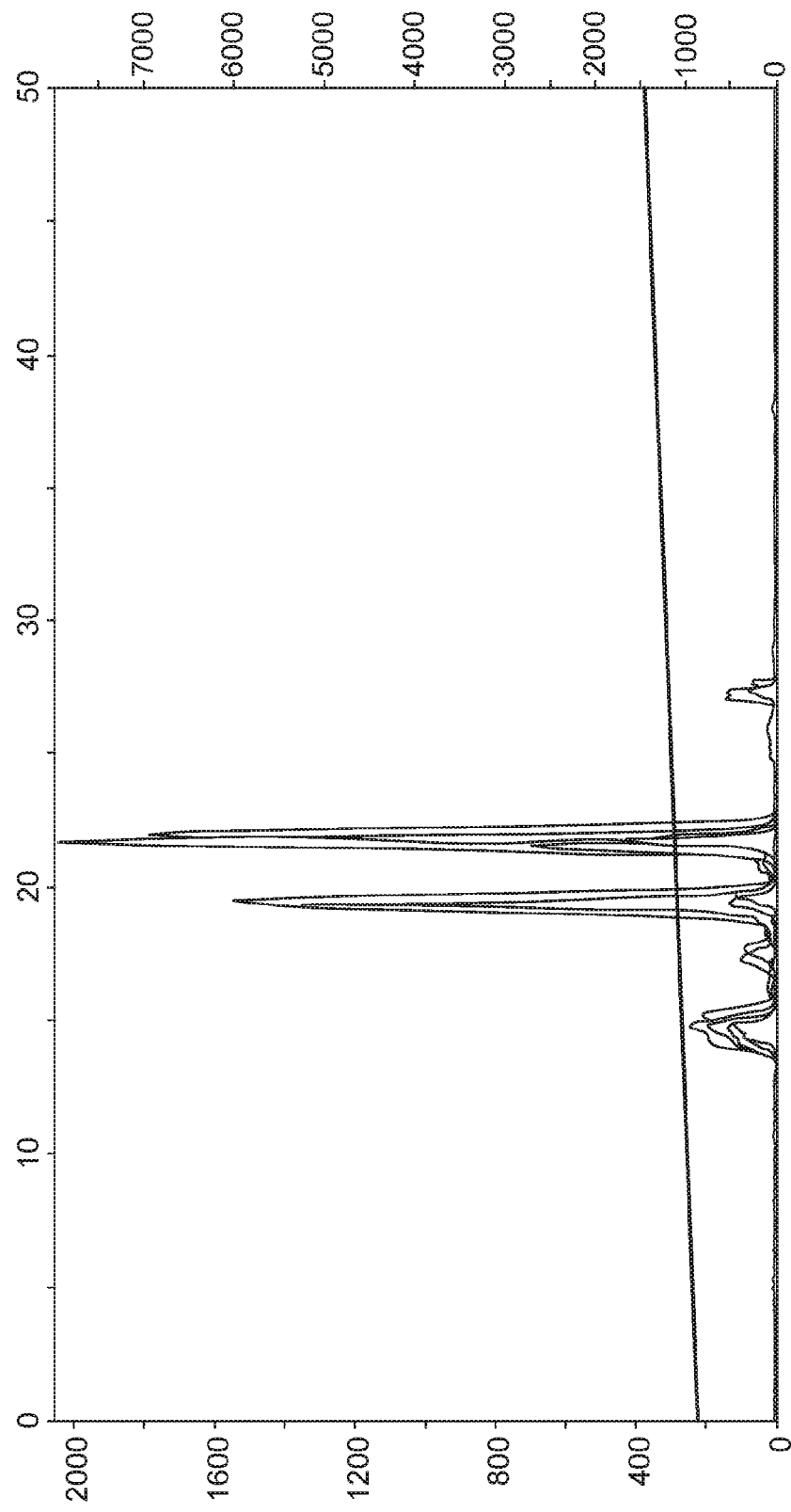

FIG. 9 shows kinetics of incorporation of nucleotide analogs (reversibly terminating dG) by Jpols 105/106/107 (SEQ ID NOs 4-6). The methodology used here is solution based assay using synthetic DNA template and synthetic primer labeled with fluorophore at 5'end. The template is specific to the nucleotide interrogated. A mixture of pre-annealed primer/template, polymerase and nucleotide are incubated at temperature appropriate for the polymerase studied. After incubation an aliquot is loaded onto capillary electrophoresis system where size separation is performed using denaturing conditions and fluorescence detection. Peaks corresponding to non-extended primer, extended primer and residual nuclease activity (primer degradation) are observed in this trace indicating polymerase ability to incorporate nucleotide analog.

Figure 10:
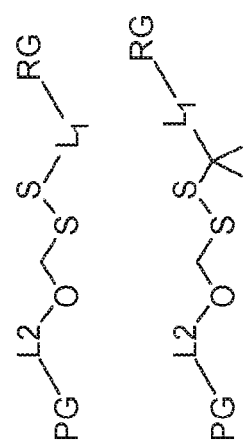

FIG. 10 shows generic universal building blocks structures comprising new cleavable linkers usable with the enzymes of the present invention. PG=Protective Group, L1, L2-linkers (aliphatic, aromatic, mixed polarity straight chain or branched). RG=Reactive Group. In one embodiment of present invention such building blocks carry an Fmoc protective group on one end of the linker and reactive NHS carbonate or carbamate on the other end. This preferred combination is particularly useful in modified nucleotides synthesis comprising new cleavable linkers. A protective group should be removable under conditions compatible with nucleic acid/nucleotides chemistry and the reactive group should be selective. After reaction of the active NHS group on the linker with amine terminating nucleotide, an Fmoc group can be easily removed using base such as piperidine or ammonia, therefore exposing amine group at the terminal end of the linker for the attachment of cleavable marker. A library of compounds comprising variety of markers can be constructed this way very quickly.

Figure 11:
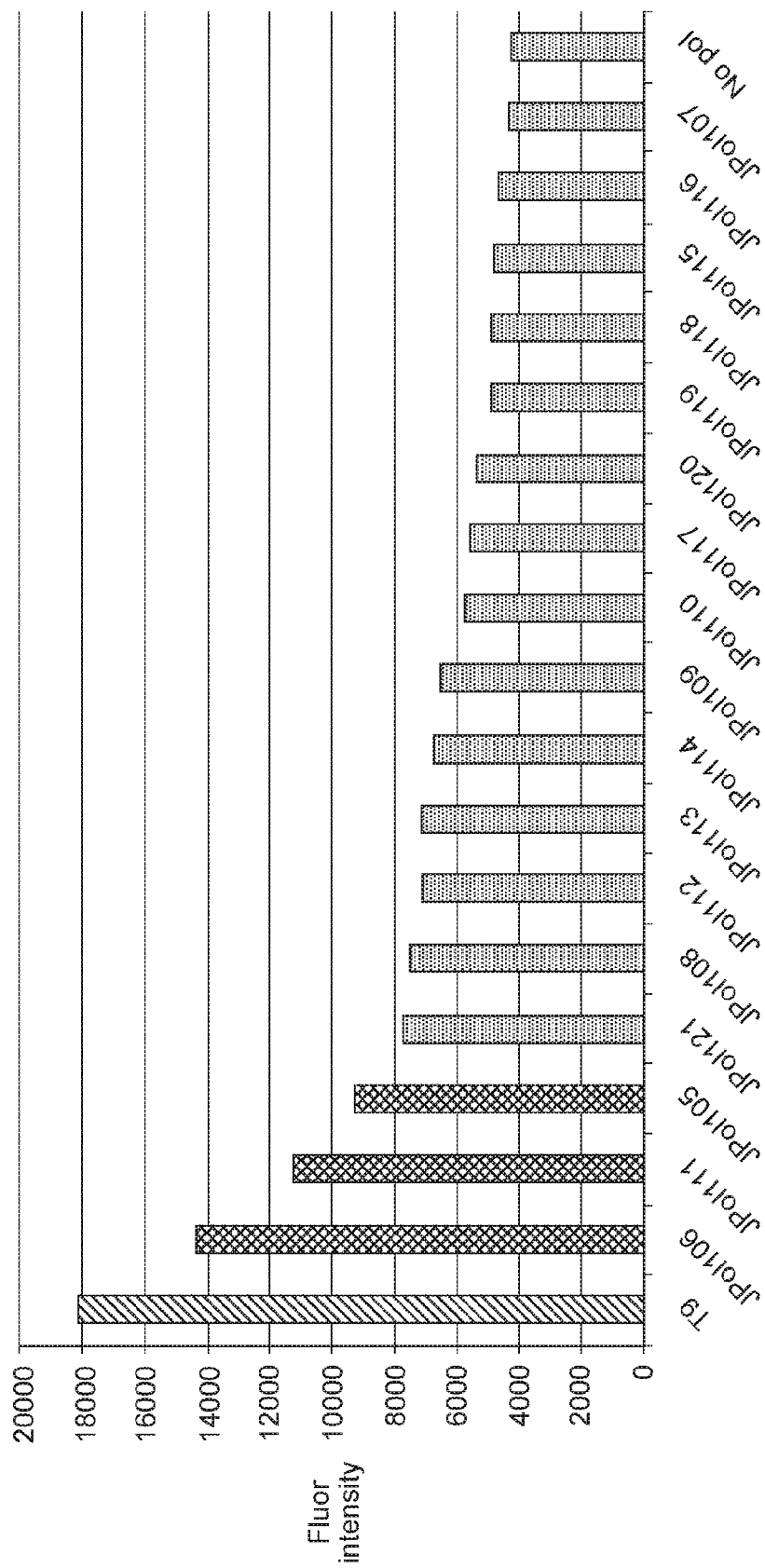

FIG. 11 shows kinetics of incorporation of nucleotide analogs (reversibly terminating dG) by Jpols 105-121 (SEQ ID NOs 4 to 20). The methodology used here is solution based assay using synthetic DNA template and synthetic primer labeled with fluorophore at 5'end. The template is specific to the nucleotide interrogated. A mixture of pre-annealed primer/template, polymerase and nucleotide are incubated at temperature appropriate for the polymerase studied. After incubation an aliquot is loaded onto capillary electrophoresis system where size separation is performed using denaturing conditions and fluorescence detection. Peaks corresponding to non-extended primer, extended primer and residual nuclease activity (primer degradation) are observed in this trace indicating polymerase ability to incorporate nucleotide analog.

EXAMPLES

| EnzymeSequences | |
| --- | --- |
| SEQ ID NO. 1<br>Wild type<br>9° N<br>*Thermococcus*<br>sp. | MILDTDYITENGKPVIRVFKKENGEFKIEYDRTFEPYFYALLK<br>DDSAIEDVKKVTAKRHGTVVKVKRAEKVQKKFLGRPIEVWK<br>LYFNHPQDVPAIRDRIRAHPAVVDIYEYDIPFAKRYLIDKGLIP<br>MEGDEELTMLAFDIETLYHEGEEFGTGPILMISYADGSEARVI<br>TWKKIDLPYVDVVSTEKEMIKRFLRVVREKDPDVLITYNGDN<br>FDFAYLKKRCEELGIKFTLGRDGSEPKIQRMGDRFAVEVKGRI<br>HFDLYPVIRRTINLPTYTLEAVYEAVFGKPKEKVYAEEIAQA<br>WESGEGLERVARYSMEDAKVTYELGREFFPMEAQLSRLIGQS<br>LWDVSRSSTGNLVEWFLLRKAYKRNELAPNKPDERELARRR<br>GGYAGGYVKEPERGLWDNIVYLDFRSLYPSIIITHNVSPDTLN<br>REGCKEYDVAPEVGHKFCKDFPGFIPSLLGDLLEERQKIKRK<br>MKATVDPLEKKLLDYRQRAIKILANSFYGYYGYAKARWYCK<br>ECAESVTAWGREYIEMVIRELEEKFGFKVLYADTDGLHATIP<br>GADAETVKKKAKEFLKYINPKLPGLLELEYEGFYVRGFFVTK<br>KKYAVIDEEGKITTRGLEIVRRDWSEIAKETQARVLEAILKHG<br>DVEEAVRIVKEVTEKLSKYEVPPEKLVIHEQITRDLRDYKATG<br>PHVAVAKRLAARGVKIRPGTVISYIVLKGSGRIGDRAIPADEF<br>DPTKHRYDAEYYIENQVLPAVERILKAFGYRKEDLRYQKTKQ<br>VGLGAWLKV |
| SEQ ID NO. 2<br>>9degN JPOL5<br>(E141A/D143A/<br>D315A/L408S/<br>Y409G/P410S/<br>A485L) | MILDTDYITENGKPVIRVFKKENGEFKIEYDRTFEPYFYALLK<br>DDSAIEDVKKVTAKRHGTVVKVKRAEKVQKKFLGRPIEVWK<br>LYFNHPQDVPAIRDRIRAHPAVVDIYEYDIPFAKRYLIDKGLIP<br>MEGDEELTMLAFAIATLYHEGEEFGTGPILMISYADGSEARVI<br>TWKKIDLPYVDVVSTEKEMIKRFLRVVREKDPDVLITYNGDN<br>FDFAYLKKRCEELGIKFTLGRDGSEPKIQRMGDRFAVEVKGRI<br>HFDLYPVIRRTINLPTYTLEAVYEAVFGKPKEKVYAEEIAQA<br>WESGEGLERVARYSMEAAKVTYELGREFFPMEAQLSRLIGQS<br>LWDVSRSSTGNLVEWFLLRKAYKRNELAPNKPDERELARRR<br>GGYAGGYVKEPERGLWDNIVYLDFRSSGSSIIITHNVSPDTLN<br>REGCKEYDVAPEVGHKFCKDFPGFIPSLLGDLLEERQKIKRK<br>MKATVDPLEKKLLDYRQRLIKILANSFYGYYGYAKARWYCK<br>ECAESVTAWGREYIEMVIRELEEKFGFKVLYADTDGLHATTP<br>GADAETVKKKAKEFLKYINPKLPGLLELEYEGFYVRGFFVTK<br>KKYAVIDEEGKITTRGLEIVRRDWSEIAKETQARVLEAILKHG<br>DVEEAVRIVKEVTEKLSKYEVPPEKLVIHEQITRDLRDYKATG<br>PHVAVAKRLAARGVKIRPGTVISYIVLKGSGRIGDRAIPADEF<br>DPTKHRYDAEYYIENQVLPAVERILKAFGYRKEDLRYQKTKQ<br>VGLGAWLKVKGKK |

-continued

EnzymeSequences

SEQ ID NO. 3  MILDTDYITENGKPVIRVFKKENGEFKIEYDRTFEPYFYALLK
9degN JPOL8   DDSA1EDVKKVTAKRHGTVVKVKRAEKVQKKFLGRPIEVWK
(E141A/D143A/ LYFNHPQDVPATRDRIRAHPAVVDTVEYDIPFAKRYLIDKGLIP
L408S/Y409G/  MEGDEELTMLAFAIATLYHEGEEFGTGPILMISYADGSEARVI
P410S/A485L)  TWKKIDLPYVDVVSTEKEMIKRFLRVVREKDPDVLITYNGDN
              FDFAYLKKRCEELGIKFTLGRDGSEPKIQRMGDRFAVEVKGRI
              HFDLYPVIRRTINLPTYTLEAVYEAVFGKPKEKVYAEEIAQA
              WESGEGLERVARYSMEDAKVTYELGREFFPMEAQLSRLIGQS
              LWDVSRSSTGNLVEWFLLRKAYKRNELAPNKPDERELARRR
              GGYAGGYVKEPERGLWDNIVYLDFRSSGSSIIITHNVSPDTLN
              REGCKEYDVAPEVGHKFCKDFPGFIPSLLGDLLEERQKIKRK
              MKATVDPLEKKLLDYRQRLIKILANSFYGYYGYAKARWYCK
              ECAESVTAWGREYIEMVIRELEEKFGFKVLYADTDGLHATIP
              GADAETVKKKAKEFLKYINPKLPGLLELEYEGFYVRGFFVTK
              KKYAVIDEEGKITTRGLEIVRRDWSEIAKETQARVLEAILKHG
              DVEEAVRIVKEVTEKLSKYEVPPEKLVIHEQITRDLRDYKATG
              PHVAVAKRLAARGVKIRPGTVISYIVLKGSGRIGDRAIPADEF
              DPTKHRYDAEYYIENQVLPAVERILKAFGYRKEDLRYQKTKQ
              VGLGAWLKVKGKK SEQ ID NO. 4  MILDTDYITENGKPVIRVFKKENGEFKIEYDRTFEPYFYALLK
9degN JPOL105 DDSAIEDVKKVTAKRHGTVVKVKRAEKVQKKFLGRPIEVWK
(E141A/D143A/ LYFNHPQDVPAIRDRIRAHPAVVDIYEYDIPFAKRYLIDKGLIP
L408H/Y409T/  MEGDEELTMLAFAIATLYHEGEEFGTGPILMISYADGSEARVI
P410C/A485L)  TWKKIDLPYVDVVSTEKEM1KRFLRVVREKDPDVLITYNGDN
              FDFAYLKKRCEELGIKFTLGRDGSEPKIQRMGDRFAVEVKGRI
              HFDLYPVIRRTINLPTYTLEAVYEAVFGKPKEKVYAEEIAQA
              WESGEGLERVARYSMEDAKVTYELGREFFPMEAQLSRLIGQS
              LWDVSRSSTGNLVEWFLLRKAYKRNELAPNKPDERELARRR
              GGYAGGYVKEPERGLWDNIVYLDFRSHTCSIIITHNVSPDTLN
              REGCKEYDVAPEVGHKFCKDFPGFIPSLLGDLLEERQKIKRK
              MKATVDPLEKKLLDYRQRLIKILANSFYGYYGYAKARWYCK
              ECAESVTAWGREYIEMVIRELEEKFGFKVLYADTDGLHATIP
              GADAETVKKKAKEFLKYINPKLPGLLELEYEGFYVRGFFVTK
              KKYAVIDEEGKITTRGLEIVRRDWSEIAKETQARVLEAILKHG
              DVEEAVRIVKEVTEKLSKYEVPPEKLVIHEQITRDLRDYKATG
              PHVAVAKRLAARGVKIRPGTVISYIVLKGSGRIGDRAIPADEF
              DPTKHRYDAEYYIENQVLPAVERILKAFGYRKEDLRYQKTKQ
              VGLGAWLKVKGKK SEQ ID NO. 5  MILDTDYITENGKPVIRVFKKENGEFKIEYDRTFEPYFYALLK
9degN JPOL106 DDSAIEDVKKVTAKRHGTVVKVKRAEKVQKKFLGRPIEVWK
(E141A/D143A/ LYFNHPQDVPAIRDRIRAHPAVVDIYEYDIPFAKRYLIDKGLIP
L408M/Y409T/  MEGDEELTMLAFAIATLYHEGEEFGTGPILMISYADGSEARVI
P410C/A485L)  TVVKKIDLPYVDVVSTEKEMIKRFLRVVREKDPDVLITYNGDN
              FDFAYLKKRCEELGIKFTLGRDGSEPKIQRMGDRFAVEVKGRI
              HFDLYPVIRRTINLPTYTLEAVYEAVFGKPKEKVYAEEIAQA
              WESGEGLERVARYSMEDAKVTYELGREFFPMEAQLSRLIGQS
              LWDVSRSSTGNLVEWFLLRKAYKRNELAPNKPDERELARRR
              GGYAGGYVKEPERGLWDNIVYLDFRSMTCSIIITHNVSPDTLN
              REGCKEYDVAPEVGHKFCKDFPGFIPSLLGDLLEERQKIKRK
              MKATVDPLEKKLLDYRQRLIKILANSFYGYYGYAKARWYCK
              ECAESVTAWGREYIEMVIRELEEKFGFKVLYADTDGLHATIP
              GADAETVKKKAKEFLKYTNPKLPGLLELEYEGFYVRGFFVTK
              KKYAVIDEEGKITTRGLEIVRRDWSEIAKETQARVLEAILKHG
              DVEEAVRIVKEVTEKLSKYEVPPEKLVIHEQITRDLRDYKATG
              PHVAVAKRLAARGVKIRPGTVISYIVLKGSGRIGDRAIPADEF
              DPTKHRYDAEYYIENQVLPAVERILKAFGYRKEDLRYQKTKQ
              VGLGAWLKVKGKK SEQ ID NO. 6  MILDTDYITENGKPVIRVFKKENGEFKIEYDRTFEPYFYALLK
9degN JPOL107 DDSAIEDVKKVTAKRHGTVVKVKRAEKVQKKFLGRPIEVWK
(E141A/D143A/ LYFNHPQDVPAIRDRIRAHPAVVDIYEYDIPFAKRYLIDKGLIP
L408G/Y409T/  MEGDEELTMLAFAIATLYHEGEEFGTGPILMISYADGSEARVI
P410F/A485L)  TWKKIDLPYVDVVSTEKEMIKRFLRVVREKDPDVLITYNGDN
              FDFAYLKKRCEELGIKFTLGRDGSEPKIQRMGDRFAVEVKGRI
              HFDLYPVIRRTINLPTYTLEAVYEAVFGKPKEKVYAEEIAQA
              WESGEGLERVARYSMEDAKVTYELGREFFPMEAQLSRLIGQS
              LWDVSRSSTGNLVEWFLLRKAYKRNELAPNKPDERELARRR
              GGYAGGYVKEPERGLWDNIVYLDFRSGTFSIIITHNVSPDTLN
              REGCKEYDVAPEVGHKFCKDFPGFIPSLLGDLLEERQKIKRK
              MKATVDPLEKKLLDYRQRLIKILANSFYGYYGYAKARWYCK
              ECAESVTAWGREYIEMVIRELEEKFGFKVLYADTDGLHATIP
              GADAETVKKKAKEFLKYINPKLPGLLELEYEGFYVRGFFVTK
              KKYAVIDEEGKITTRGLEIVRRDWSE1AKETQARVLEAILKHG
              DVEEAVRIVKEVTEKLSKYEVPPEKLVIHEQTTRDLRDYKATG -continued

| EnzymeSequences |
|---|
| | PHVAVAKRLAARGVKIRPGTVISYIVLKGSGRIGDRAIPADEF<br>DPTKHRYDAEYYIENQVLPAVERILKAFGYRKEDLRYQKTKQ<br>VGLGAWLKVKGKK |
| SEQ ID NO. 7<br>9degN JPOL108<br>(E141A/D143A/<br>L408G/Y409T/<br>P410C/A485L) | MILDTDYITENGKPVIRVFKKENGEFKIEYDRTFEPYFYALLK<br>DDSAIEDVKKVTAKRHGTVVKVKRAEKVQKKFLGRPIEVWK<br>LYFNHPQDVPAIRDRIRAHPAVVDIYEYDIPFAKRYLIDKGLIP<br>MEGDEELTMLAFAIATLYHEGEEFGTGPILMISYADGSEARVI<br>TWKKIDLPYVDVVSTEKEMIKRFLRVVREKDPDVL1TYNGDN<br>FDFAYLKKRCEELGIKFTLGRDGSEPKIQRMGDRFAVEVKGRI<br>HFDLYPVIRRTINLPTYTLEAVYEAVFGKPKEKVYAEEIAQA<br>WESGEGLERVARYSMEDAKVTYELGREFFPMEAQLSRLIGQS<br>LWDVSRSSTGNLVEWFLLRKAYKRNELAPNKPDERELARRR<br>GGYAGGYVKEPERGLWDNIVYLDFRSGTCSIIITHNVSPDTLN<br>REGCKEYDVAPEVGHKFCKDFPGFTPSLLGDLLEERQKIKRK<br>MKATVDPLEKKLLDYRQRLIKILANSFYGYYGYAKARWYCK<br>ECAESVTAWGREYIEMVIRELEEKFGFKVLYADTDGLHATIP<br>GADAETVKKKAKEFLKYINPKLPGLLELEYEGFYVRGFFVTK<br>KKYAVIDEEGKITTRGLEIVRRDWSEIAKETQARVLEAILKHG<br>DVEEAVRIVKEVTEKLSKYEVPPEKLVIHEQITRDLRDYKATG<br>PHVAVAKRLAARGVKIRPGTVISYIVLKGSGRIGDRAIPADEF<br>DPTKHRYDAEYYIENQVLPAVERILKAFGYRKEDLRYQKTKQ<br>VGLGAWLKVKGKK |
| SEQ ID NO. 8<br>9degN JPOL109<br>(E141A/D143A/<br>L408N/Y409T/<br>P410C/A485L) | MILDTDYITENGKPVIRVFKKENGEFKIEYDRTFEPYFYALLK<br>DDSAIEDVKKVTAKRHGTVVKVKRAEKVQKKFLGRPIEVWK<br>LYFNHPQDVPAIRDRIRAHPAVVDIYEYDIPFAKRYLIDKGLIP<br>MEGDEELTMLAFAIATLYHEGEEFGTGPILMISYADGSEARVI<br>TWKKIDLPYVDVVSTEKEMIKRFLRVVREKDPDVLITYNGDN<br>FDFAYLKKRCEELGIKFTLGRDGSEPKIQRMGDRFAVEVKGRI<br>HFDLYPVIRRTINLPTYTLEAVYEAVFGKPKEKVYAEEIAQA<br>WESGEGLERVARYSMEDAKVTYELGREFFPMEAQLSRLIGQS<br>LWDVSRSSTGNLVEWFLLRKAYKRNELAPNKPDERELARRR<br>GGYAGGYVKEPERGLWDNIVYLDFRSNTCSIIITHNVSPDTLN<br>REGCKEYDVAPEVGHKFCKDFPGFIPSLLGDLLEERQKIKRK<br>MKATVDPLEKKLLDYRQRLIKILANSFYGYYGYAKARWYCK<br>ECAESVTAWGREYIEMVIRELEEKFGFKVLYADTDGLHATIP<br>GADAETVKKKAKEFLKYINPKLPGLLELEYEGFYVRGFFVTK<br>KKYAVIDEEGKITTRGLEIVRRDWSEIAKETQARVLEAILKHG<br>DVEEAVRIVKEVTEKLSKYEVPPEKLVIHEQITRDLRDYKATG<br>PHVAVAKRLAARGVKIRPGTVISYIVLKGSGRIGDRAIPADEF<br>DPTKHRYDAEYYIENQVLPAVERILKAFGYRKEDLRYQKTKQ<br>VGLGAWLKVKGKK |
| SEQ ID NO. 9<br>9degN JPOL110<br>(E141A/D143A/<br>L408G/Y409T/<br>P410N/A485L) | MILDTDYITENGKPVIRVFKKENGEFKIEYDRTFEPYFYALLK<br>DDSAIEDVKKVTAKRHGTVVKVKRAEKVQKKFLGRPIEVWK<br>LYFNHPQDVPAIRDRIRAHPAVVDIYEYDIPFAKRYLIDKGLIP<br>MEGDEELTMLAFAIATLYHEGEEFGTGPILMISYADGSEARVI<br>TWKKIDLPYVDVVSTEKEMIKRFLRVVREKDPDVLITYNGDN<br>FDFAYLKKRCEELGIKFTLGRDGSEPKIQRMGDRFAVEVKGRI<br>HFDLYPVIRRTINLPTYTLEAVYEAVFGKPKEKVYAEEIAQA<br>WESGEGLERVARYSMEDAKVTYELGREFFPMEAQLSRLIGQS<br>LWDVSRSSTGNLVEWFLLRKAYKRNELAPNKPDERELARRR<br>GGYAGGYVKEPERGLWDNIVYLDFRSGTNSIIITHNVSPDTLN<br>REGCKEYDVAPEVGHKFCKDFPGFIPSLLGDLLEERQKIKRK<br>MKATVDPLEKKLLDYRQRLIKILANSFYGYYGYAKARWYCK<br>ECAESVTAWGREYIEMVIRELEEKFGFKVLYADTDGLHATIP<br>GADAETVKKKAKEFLKYINPKLPGLLELEYEGFYVRGFFVTK<br>KKYAVIDEEGKITTRGLEIVRRDWSEIAKETQARVLEAILKHG<br>DVEEAVRIVKEVTEKLSKYEVPPEKLVIHEQITRDLRDYKATG<br>PHVAVAKRLAARGVKIRPGTVISYIVLKGSGRIGDRAIPADEF<br>DPTKHRYDAEYYIENQVLPAVERILKAFGYRKEDLRYQKTKQ<br>VGLGAWLKVKGKK |
| SEQ ID NO. 10<br>9degN JPOL111<br>(E141A/D143A/<br>L408T/Y409T/<br>P410C/A485L) | MILDTDYITENGKPVIRVFKKENGEFKIEYDRTFEPYFYALLK<br>DDSAIEDVKKVTAKRHGTVVKVKRAEKVQKKFLGRPIEVWK<br>LYFNHPQDVPAIRDRIRAHPAVVDIYEYDIPFAKRYLIDKGLIP<br>MEGDEELTMLAFAIATLYHEGEEFGTGPILMISYADGSEARVI<br>TWKKIDLPYVDVVSTEKEMIKRFLRVVREKDPDVLITYNGDN<br>FDFAYLKKRCEELGIKFTLGRDGSEPKIQRMGDRFAVEVKGRI<br>HFDLYPVIRRTINLPTYTLEAVYEAVFGKPKEKVYAEEIAQA<br>WESGEGLERVARYSMEDAKVTYELGREFFPMEAQLSRLIGQS<br>LWDVSRSSTGNLVEWFLLRKAYKRNELAPNKPDERELARRR<br>GGYAGGYVKEPERGLWDNIVYLDFRSTTCSIIITHNVSPDTLN<br>REGCKEYDVAPEVGHKFCKDFPGFIPSLLGDLLEERQKIKRK<br>MKATVDPLEKKLLDYRQRLIKILANSFYGYYGYAKARWYCK<br>ECAESVTAWGREYIEMVIRELEEKFGFKVLYADTDGLHATIP |

| EnzymeSequences |
|---|
| GADAETVKKKAKEFLKYINPKLPGLLELEYEGFYVRGFFVTK<br>KKYAVIDEEGKITTRGLEIVRRDWSEIAKETQARVLEAILKHG<br>DVEEAVRIVKEVTEKLSKYEVPPEKLVIHEQITRDLRDYKATG<br>PHVAVAKRLAARGVKIRPGTVISYIVLKGSGRIGDRAIPADEF<br>DPTKHRYDAEYYIENQVLPAVERTLKAFGYRKEDLRYQKTKQ<br>VGLGAWLKVKGKK |

| SEQ ID NO. 11<br>9degN JPOL112<br>(E141A/D143A/<br>L408H/Y409V/<br>P410C/A485L) | MILDTDYITENGKPVIRVFKKENGEFKIEYDRTFEPYFYALLK<br>DDSAIEDVKKVTAKRHGTVVKVKRAEKVQKKFLGRPIEVWK<br>LYFNHPQDVPAIRDRIRAHPAVVDIYEYDIPFAKRYLIDKGLIP<br>MEGDEELTMLAFAIATLYHEGEEFGTGPILMISYADGSEARVI<br>TWKKIDLPYVDVVSTEKEMIKRFLRVVREKDPDVLITYNGDN<br>FDFAYLKKRCEELGIKFTLGRDGSEPKIQRIVIGDRFAVEVKGRIHFD<br>LYPVIRRTINLPTYTLEAVYEAVFGKPKEKVYAEEIAQA<br>WESGEGLERVARYSMEDAKVTYELGREFFPMEAQLSRLIGQS<br>LWDVSRSSTGNLVEWFLLRKAYKRNELAPNKPDERELARRR<br>GGYAGGYVKEPERGLWDNIVYLDFRSHVCSIIITHNVSPDTLN<br>REGCKEYDVAPEVGHKFCKDFPGFIPSLLGDLLEERQK1KRK<br>MKATVDPLEKKLLDYRQRLIKILANSFYGYYGYAKARWYCK<br>ECAESVTAWGREYIEMVIRELEEKFGFKVLYADTDGLHATIP<br>GADAETVKKKAKEFLKYINPKLPGLLELEYEGFYVRGFFVTK<br>KKYAVIDEEGKITTRGLEIVRRDWSEIAKETQARVLEAILKHG<br>DVEEAVRIVKEVTEKLSKYEVPPEKLVIHEQITRDLRDYKATG<br>PHVAVAKRLAARGVKIRPGTVISYIVLKGSGRIGDRAIPADEF<br>DPTKHRYDAEYYIENQVLPAVERILKAFGYRKEDLRYQKTKQ<br>VGLGAWLKVKGKK |
| SEQ ID NO. 12<br>9degN JPOL113<br>(E141A/D143A/<br>L408M/Y409V/<br>P410C/A485L) | MILDTDY1TENGKPV1RVFKKENGEFK1EYDRTFEPYFYALLK<br>DDSATEDVKKVTAKRHGTVVKVKRAEKVQKKFLGRPIEVWK<br>LYFNHPQDVPAIRDRIRAHPAVVDIYEYDIPFAKRYLIDKGLIP<br>MEGDEELTMLAFAIATLYHEGEEFGTGPILMISYADGSEARVI<br>TWKKIDLPYVDVVSTEKEMIKRFLRVVREKDPDVLITYNGDN<br>FDFAYLKKRCEELGIKFTLGRDGSEPKIQRMGDRFAVEVKGRI<br>HFDLYPVIRRTINLPTYTLEAVYEAVFGKPKEKVYAEEIAQA<br>WESGEGLERVARYSMEDAKVTYELGREFFPMEAQLSRLIGQS<br>LWDVSRSSTGNLVEWFLLRKAYKRNELAPNKPDERELARRR<br>GGYAGGYVKEPERGLWDNIVYLDFRSMVCSIIITHNVSPDTL<br>NREGCKEYDVAPEVGHKFCKDFPGFIPSLLGDLLEERQIUKRK<br>MKATVDPLEKKLLDYRQRLIKILANSFYGYYGYAKARWYCK<br>ECAESVTAWGREYIEMVIRELEEKFGFKVLYADTDGLHATIP<br>GADAETVKKKAKEFLKYINPKLPGLLELEYEGFYVRGFFVTK<br>KKYAVIDEEGKITTRGLEIVRRDWSEIAKETQARVLEAILKHG<br>DVEEAVRIVKEVTEKLSKYEVPPEKLVIHEQITRDLRDYKATG<br>PHVAVAKRLAARGVKIRPGTVISYIVLKGSGRIGDRAIPADEF<br>DPTKHRYDAEYYIENQVLPAVERILKAFGYRKEDLRYQKTKQ<br>VGLGAWLKVKGKK |
| SEQ ID NO. 13<br>9degN JPOL114<br>(E141A/D143A/<br>L408T/Y409V/<br>P410C/A485L) | MILDTDYITENGKPVIRVFKKENGEFKIEYDRTFEPYFYALLK<br>DDSAIEDVKKVTAKRHGTVVKVKRAEKVQKKFLGRPIEVWK<br>LYFNHPQDVPAIRDRIRAHPAVVDIYEYDIPFAKRYLIDKGLIP<br>MEGDEELTMLAFAIATLYHEGEEFGTGPILMISYADGSEARVI<br>TVVKKIDLPYVDVVSTEKEMIKRFLRVVREKDPDVLITYNGDN<br>FDFAYLKKRCEELGIKFTLGRDGSEPKIQRMGDRFAVEVKGRI<br>HFDLYPVIRRTINLPTYTLEAVYEAVFGKPKEKVYAEEIAQA<br>WESGEGLERVARYSMEDAKVTYELGREFFPMEAQLSRLIGQS<br>LWDVSRSSTGNLVEWFLLRKAYKRNELAPNKPDERELARRR<br>GGYAGGYVKEPERGLWDN1VYLDFRSTVCSIIITHNVSPDTLN<br>REGCKEYDVAPEVGHKFCKDFPGFTPSLLGDLLEERQIKRK<br>MKATVDPLEKKLLDYRQRLIKILANSFYGYYGYAKARWYCK<br>ECAESVTAWGREYIEMVIRELEEKFGFKVLYADTDGLHATIP<br>GADAETVKKKAKEFLKYINPKLPGLLELEYEGFYVRGFFVTK<br>KKYAVIDEEGKITTRGLEIVRRDWSEIAKETQARVLEAILKHG<br>DVEEAVRIVKEVTEKLSKYEVPPEKLVIHEQITRDLRDYKATG<br>PHVAVAKRLAARGVKIRPGTVISYIVLKGSGRIGDRAIPADEF<br>DPTKHRYDAEYYIENQVLPAVERILKAFGYRKEDLRYQKTKQ<br>VGLGAWLKVKGKK |
| SEQ ID NO. 14<br>9degN JPOL115<br>(E141A/D143A/<br>L408H/Y409V/<br>P410D/A485L) | MILDTDYITENGKPVIRVFKKENGEFKIEYDRTFEPYFYALLK<br>DDSAIEDVKKVTAKRHGTVVKVKRAEKVQKKFLGRPIEVWK<br>LYFNHPQDVPAIRDRIRAHPAVVDIYEYDIPFAKRYLIDKGLIP<br>MEGDEELTMLAFAIATLYHEGEEFGTGPILMISYADGSEARVI<br>TWKKIDLPYVDVVSTEKEMIKRFLRVVREKDPDVLITYNGDN<br>FDFAYLKKRCEELGIKFTLGRDGSEPKIQRMGDRFAVEVKGRI<br>HFDLYPVIRRTINLPTYTLEAVYEAVFGKPKEKVYAEEIAQA<br>WESGEGLERVARYSMEDAKVTYELGREFFPMEAQLSRLIGQS<br>LWDVSRSSTGNLVEWFLLRKAYKRNELAPNKPDERELARRR<br>GGYAGGYVKEPERGLWDNIVYLDFRSHVDSIIITHNVSPDTLN |

| EnzymeSequences |
|---|
| REGCKEYDVAPEVGHKFCKDFPGFIPSLLGDLLEERQKIKRK<br>MKATVDPLEKKLLDYRQRLIKILANSFYGYYGYAKARWYCK<br>ECAESVTAWGREYIEMVIRELEEKFGFKVLYADTDGLHATIP<br>GADAETVKKKAKEFLKYINPKLPGLLELEYEGFYVRGFFVTK<br>KKYAVIDEEGKITTRGLEIVRRDWSEIAKETQARVLEAILKHG<br>DVEEAVRIVKEVTEKLSKYEVPPEKLVIHEQITRDLRDYKATG<br>PHVAVAKRLAARGVKIRPGTVISYIVLKGSGRIGDRAIPADEF<br>DPTKHRYDAEYYIENQVLPAVERILKAFGYRKEDLRYQKTKQ<br>VGLGAWLKVKGKK |
| SEQ ID NO. 15<br>9degN JPOL116<br>(E141A/D143A/<br>L408M/Y409V/<br>P410D/A485L) | MILDTDYITENGKPVIRVFKKENGEFKIEYDRTFEPYFYALLK<br>DDSAIEDVKKVTAKRHGTVVKVKRAEKVQKKFLGRPIEVWK<br>LYFNHPQDVPAIRDRIRAHPAVVDIYEYDIPFAKRYLIDKGLIP<br>MEGDEELTMLAFAIATLYHEGEEFGTGPILMISYADGSEARVI<br>TWKKIDLPYVDVVSTEKEMIKRFLRVVREKDPDVLITYNGDN<br>FDFAYLKKRCEELGIKFTLGRDGSEPKIQRMGDRFAVEVKGRI<br>HFDLYPVIRRTINLPTYTLEAVYEAVFGKPKEKVYAEEIAQA<br>WESGEGLERVARYSMEDAKVTYELGREFFPMEAQLSRLIGQS<br>LWDVSRSSTGNLVEWFLLRKAYKRNELAPNKPDERELARRR<br>GGYAGGYVKEPERGLWDNIVYLDFRSMVDSIIITHNVSPDTL<br>NREGCKEYDVAPEVGHKFCKDFPGFIPSLLGDLLEERQKIKRK<br>MKATVDPLEKKLLDYRQRLIKILANSFYGYYGYAKARWYCK<br>ECAESVTAWGREYIEMVIRELEEKFGFKVLYADTDGLHATIP<br>GADAETVKKKAKEFLKYINPKLPGLLELEYEGFYVRGFFVTK<br>KKYAVIDEEGKITTRGLEIVRRDWSEIAKETQARVLEAILKHG<br>DVEEAVRIVKEVTEKLSKYEVPPEKLVIHEQITRDLRDYKATG<br>PHVAVAKRLAARGVKIRPGTVISYIVLKGSGRIGDRAIPADEF<br>DPTKHRYDAEYYIENQVLPAVERILKAFGYRKEDLRYQKTKQ<br>VGLGAWLKVKGKK |
| SEQ ID NO. 16<br>9degN JPOL117<br>(E141A/D143A/<br>L408M/Y409V/<br>P410D/A485L) | MILDTDYITENGKPVIRVFKKENGEFKIEYDRTFEPYFYALLK<br>DDSAIEDVKKVTAKRHGTVVKVKRAEKVQKKFLGRPIEVWK<br>LYFNHPQDVPAIRDRIRAHPAVVDIYEYDIPFAKRYLIDKGLIP<br>MEGDEELTMLAFAIATLYHEGEEFGTGPILMISYADGSEARVI<br>TWKKIDLPYVDVVSTEKEMIKRFLRVVREKDPDVLITYNGDN<br>FDFAYLKKRCEELGIKFTLGRDGSEPKIQRMGDRFAVEVKGRI<br>HFDLYPVIRRTINLPTYTLEAVYEAVFGKPKEKVYAEEIAQA<br>WESGEGLERVARYSMEDAKVTYELGREFFPMEAQLSRLIGQS<br>LWDVSRSSTGNLVEWFLLRKAYKRNELAPNKPDERELARRR<br>GGYAGGYVKEPERGLWDNIVYLDFRSTVDSIIITHNVSPDTLN<br>REGCKEYDVAPEVGHKFCKDFPGFIPSLLGDLLEERQKIKRK<br>MKATVDPLEKKLLDYRQRLIKILANSFYGYYGYAKARWYCK<br>ECAESVTAWGREYIEMVIRELEEKFGFKVLYADTDGLHATIP<br>GADAETVKKKAKEFLKYINPKLPGLLELEYEGFYVRGFFVTK<br>KKYAVIDEEGKITTRGLEIVRRDWSEIAKETQARVLEAILKHG<br>DVEEAVRIVKEVTEKLSKYEVPPEKLVIHEQITRDLRDYKATG<br>PHVAVAKRLAARGVKIRPGTVISYIVLKGSGRIGDRAIPADEF<br>DPTKHRYDAEYYIENQVLPAVERILKAFGYRKEDLRYQKTKQ<br>VGLGAWLKVKGKK |
| SEQ ID NO. 17<br>9degN JPOL118<br>(E141A/D143A/<br>L408H/Y409T/<br>P410Q/A485L) | MILDTDYITENGKPVIRVFKKENGEFKIEYDRTFEPYFYALLK<br>DDSAIEDVKKVTAKRHGTVVKVKRAEKVQKKFLGRPIEVWK<br>LYFNHPQDVPAIRDRIRAHPAVVDIYEYDIPFAKRYLIDKGLIP<br>MEGDEELTMLAFAIATLYHEGEEFGTGPILMISYADGSEARVI<br>TWKKIDLPYVDVVSTEKEMIKRFLRVVREKDPDVLITYNGDN<br>FDFAYLKKRCEELGIKFTLGRDGSEPKIQRMGDRFAVEVKGRI<br>HFDLYPVIRRTINLPTYTLEAVYEAVFGKPKEKVYAEEIAQA<br>WESGEGLERVARYSMEDAKVTYELGREFFPMEAQLSRLIGQS<br>LWDVSRSSTGNLVEWFLLRKAYKRNELAPNKPDERELARRR<br>GGYAGGYVKEPERGLWDNIVYLDFRSHTQSIIITHNVSPDTLN<br>REGCKEYDVAPEVGHKFCKDFPGFIPSLLGDLLEERQKIKRK<br>MKATVDPLEKKLLDYRQRLIKILANSFYGYYGYAKARWYCK<br>ECAESVTAWGREYIEMVIRELEEKFGFKVLYADTDGLHATIP<br>GADAETVKKKAKEFLKYINPKLPGLLELEYEGFYVRGFFVTK<br>KKYAVIDEEGKITTRGLEIVRRDWSEIAKETQARVLEAILKHG<br>DVEEAVRIVKEVTEKLSKYEVPPEKLVIHEQITRDLRDYKATG<br>PHVAVAKRLAARGVKIRPGTVISYIVLKGSGRIGDRAIPADEF<br>DPTKHRYDAEYYIENQVLPAVERILKAFGYRKEDLRYQKTKQ<br>VGLGAWLKVKGKK |
| SEQ ID NO. 18<br>9degN JPOL119<br>(E141A/D143A/<br>L408M/Y409T/<br>P410Q/A485L) | MILDTDYITENGKPVIRVFKKENGEFKIEYDRTFEPYFYALLK<br>DDSAIEDVKKVTAKRHGTVVKVKRAEKVQKKFLGRPIEVWK<br>LYFNHPQDVPAIRDRIRAHPAVVDIYEYDIPFAKRYLIDKGLIP<br>MEGDEELTMLAFAIATLYHEGEEFGTGPILMISYADGSEARVI<br>TWKKIDLPYVDVVSTEKEMIKRFLRVVREKDPDVLITYNGDN<br>FDFAYLKKRCEELGIKFTLGRDGSEPKIQRMGDRFAVEVKGRI<br>HFDLYPVIRRTINLPTYTLEAVYEAVEGKPKEKVYAEEIAQA |

| EnzymeSequences | |
|---|---|
| | WESGEGLERVARYSMEDAKVTYELGREFFPMEAQLSRLIGQS<br>LWDVSRSSTGNLVEWFLLRKAYKRNELAPNKPDERELARRR<br>GGYAGGYVKEPERGLWDNIVYLDFRSMTQSIIITHNVSPDTLN<br>REGCKEYDVAPEVGHKFCKDFPGFIPSLLGDLLEERQIUKRK<br>MKATVDPLEKKLLDYRQRLIKILANSFYGYYGYAKARWYCK<br>ECAESVTAWGREYIEMVIRELEEKFGFKVLYADTDGLHATIP<br>GADAETVKKKAKEFLKYINPKLPGLLELEYEGFYVRGFFVTK<br>KKYAVIDEEGK1TTRGLEIVRRDWSEIAKETQARVLEAILKHG<br>DVEEAVRIVKEVTEKLSKYEVPPEKLVIHEQTTRDLRDYKATG<br>PHVAVAKRLAARGVKIRPGTVISYIVLKGSGRIGDRAIPADEF<br>DPTKHRYDAEYYIENQVLPAVERILKAFGYRKEDLRYQKTKQ<br>VGLGAWLKVKGKK |
| SEQ ID NO. 19<br>9degN JPOL120<br>(E141A/D143A/<br>L408T/Y409T/<br>P410Q/A485L) | MILDTDYITENGKPVIRVEKKENGEFKIEYDRTEEPYFYALLK<br>DDSAIEDVKKVTAKRHGTVVKVKRAEKVQKKFLGRPIEVWK<br>LYFNHPQDVPAIRDRIRAHPAVVDIYEYDIPFAKRYLIDKGLIP<br>MEGDEEELTMLAFAIATLYHEGEEFGTGPILMISYADGSEARVI<br>TWKKIDLPYVDVVSTEKEMIKRFLRVVREKDPDVLITYNGDN<br>FDFAYLKKRCEELGIKFTLGRDGSEPKIQRMGDRFAVEVKGRI<br>HEDLYPVIRRTINLPTYTLEAVYEAVEGKPKEKVYAEEIAQA<br>WESGEGLERVARYSMEDAKVTYELGREFFPMEAQLSRLIGQS<br>LWDVSRSSTGNLVEWFLLRKAYKRNELAPNKPDERELARRR<br>GGYAGGYVKEPERGLWDNIVYLDFRSTTQSIIITHNVSPDTLN<br>REGCKEYDVAPEVGHKECKDEPGFIPSLLGDLLEERQKIKRK<br>MKATVDPLEKKLLDYRQRLIKILANSFYGYYGYAKARWYCK<br>ECAESVTAWGREYIEMVIRELEEKFGEKVLYADTDGLHATIP<br>GADAETVKKKAKEFLKYINPKLPGLLELEYEGFYVRGFEVTK<br>KKYAVIDEEGKITTRGLEIVRRDWSEIAKETQARVLEAILKHG<br>DVEEAVRIVKEVTEKLSKYEVPPEKLVIHEQITRDLRDYKATG<br>PHVAVAKRLAARGVKIRPGTVISYIVLKGSGRIGDRAIPADEF<br>DPTKHRYDAEYYIENQVLPAVERILKAFGYRKEDLRYQKTKQ<br>VGLGAWLKVKGKK |
| SEQ ID NO. 20<br>9degN JPOL121<br>(E141A/D143A/<br>L408M/Y409T/<br>P410Q/A485L) | MILDTDYITENGKPVIRVEKKENGEFKIEYDRTEEPYFYALLK<br>DDSAIEDVKKVTAKRHGTVVKVKRAEKVQKKFLGRPIEVWK<br>LYFNHPQDVPAIRDRIRAHPAVVDIYEYDIPFAKRYLIDKGLIP<br>MEGDEEELTMLAFAIATLYHEGEEFGTGPILMISYADGSEARVI<br>TWKKIDLPYVDVVSTEKEMIKRFLRVVREKDPDVLITYNGDN<br>FDFAYLKKRCEELGIKFTLGRDGSEPKIQRMGDRFAVEVKGRI<br>HEDLYPVIRRTINLPTYTLEAVYEAVEGKPKEKVYAEEIAQA<br>WESGEGLERVARYSMEDAKVTYELGREFFPMEAQLSRLIGQS<br>LWDVSRSSTGNLVEWFLLRKAYKRNELAPNKPDERELARRR<br>GGYAGGYVKEPERGLWDNIVYLDFRSHTNSIIITHNVSPDTLN<br>REGCKEYDVAPEVGHKECKDEPGFIPSLLGDLLEERQKIKRK<br>MKATVDPLEKKLLDYRQRLIKILANSFYGYYGYAKARWYCK<br>ECAESVTAWGREYIEMVIRELEEKFGEKVLYADTDGLHATIP<br>GADAETVKKKAKEFLKYINPKLPGLLELEYEGFYVRGFEVTK<br>KKYAVIDEEGKITTRGLEIVRRDWSEIAKETQARVLEAILKHG<br>DVEEAVRIVKEVTEKLSKYEVPPEKLVIHEQITRDLRDYKATG<br>PHVAVAKRLAARGVKIRPGTVISYIVLKGSGRIGDRAIPADEF<br>DPTKHRYDAEYYIENQVLPAVERILKAFGYRKEDLRYQKTKQ<br>VGLGAWLKVKGKK |

Example 1

Synthesis of 3'-O-(methylthiomethyl)-5'-O-(tert-butyldimethylsilyl)-2'-deoxythymidine (2)

5'-O-(tert-butyldimethylsilyl)-2'-deoxy thymidine (1) (2.0 g, 5.6 mmol) was dissolved in a mixture consisting of DMSO (10.5 mL), acetic acid (4.8 mL), and acetic anhydride (15.4 mL) in a 250 mL round bottom flask, and stirred for 48 hours at room temperature. The mixture was then quenched by adding saturated $K_2CO_3$ solution until evolution of gaseous $CO_2$ was stopped. The mixture was then extracted with EtOAc (3×100 mL) using a separating funnel. The combined organic extract was then washed with a saturated solution of $NaHCO_3$ (2×150 mL) in a partitioning funnel, and the organic layer was dried over $Na_2SO_4$. The organic part was concentrated by rotary evaporation. The reaction mixture was finally purified by silica gel column chromatography.

Example 2

Synthesis of 3'-O-(ethyldithiomethyl)-2'-deoxythymidine (4)

Compound 2 (1.75 g, 4.08 mmol), dried overnight under high vacuum, dissolved in 20 mL dry $CH_2Cl_2$ was added with EtsN (0.54 mL, 3.87 mmol) and 5.0 g molecular sieve-3A, and stirred for 30 min under Ar atmosphere. The reaction flask was then placed on an ice-bath to bring the temperature to sub-zero, and slowly added with 1.8 eq 1M $SO_2Cl_2$ in $CH_2Cl_2$ (1.8 mL) and stirred at the same temperature for 1.0 hour. Then the ice-bath was removed to bring the flask to room temperature, and added with a solution of potassium thiotosylate (1.5 g) in 4 mL dry DMF and stirred for 0.5 hour at room temperature.

Then 2 eq EtSH (0.6 mL) was added and stirred additional 40 min. The mixture was then diluted with 50 mL $CH_2Cl_2$ and filtered through celite-S in a funnel. The sample was washed with adequate amount of CH$_2$Cl$_2$ to make sure that the product was filtered out. The CH$_2$Cl$_2$ extract was then concentrated and purified by chromatography on a silica gel column (Hex:EtOAC/1:1 to 1:3, Rf=0.3 in Hex:EtOAc/1:1). The resulting crude product was then treated with 2.2 g of NH$_4$F in 20 mL MeOH. After 36 hours, the reaction was quenched with 20 mL saturated NaHCO$_3$ and extracted with CH$_2$Cl$_2$ by partitioning. The CH$_2$Cl$_2$ part was dried over Na$_2$SO$_4$ and purified by chromatography (Hex:EtOAc/1:1 to 1:2).

Example 3

Synthesis of the Triphosphate of 3'-O-(ethyldithiomethyl)-2'-deoxythymidine (5)

In a 25 mL flask, compound 4 (0.268 g, 0.769 mmol) was added with proton sponge (210 mg), equipped with rubber septum. The sample was dried under high vacuum for overnight. The material was then dissolved in 2.6 mL (MeO)$_3$PO under argon atmosphere. The flask, equipped with Ar-gas supply, was then placed on an ice-bath, stirred to bring the temperature to sub-zero. Then 1.5 equivalents of POCl$_3$ was added at once by a syringe and stirred at the same temperature for 2 hours under Argon atmosphere. Then the ice-bath was removed and a mixture consisting of tributylammonium-pyrophosphate (1.6 g) and Bu$_3$N (1.45 mL) in dry DMF (6 mL) was prepared. The entire mixture was added at once and stirred for 10 min. The reaction mixture was then diluted with TEAB buffer (30 mL, 100 mM) and stirred for additional 3 hours at room temperature. The crude product was concentrated by rotary evaporation, and purified by CI 8 Prep HPLC (method: 0 to 5 min 100% A followed by gradient up to 50% B over 72 min, A=50 mM TEAB and B=acetonitrile). After freeze drying of the target fractions, the semi-pure product was further purified by ion exchange HPLC using PL-SAX Prep column (Method: 0 to 5 min 100% A, then gradient up to 70% B over 70 min, where A=15% acetonitrile in water, B=0.85M TEAB buffer in 15% acetonitrile). Final purification was carried out by CI8 Prep HPLC as described above resulting in ~25% yield of compound 5.

Example 4

Synthesis of N$^4$-Benzoyl-5'-O-(tert-butyldimethylsilyl)-3'-O-(methylthiomethyl)-2' deoxycytidine (7)

N$^4$-benzoyl-5'-O-(tert-butyldimethylsilyl)-2'-deoxycytidine (6) (50 g, 112.2 mmol) was dissolved in DMSO (210 mL) in a 2 L round bottom flask. It was added sequentially with acetic acid (210 mL) and acetic anhydride (96 mL), and stirred for 48 h at room temperature. During this period of time, a complete conversion to product was observed by TLC (Rf=0.6, EtOAc:hex/10:1 for the product).

The mixture was separated into two equal fractions, and each was transferred to a 2000 mL beaker and neutralized by slowly adding saturated K$_2$CO$_3$ solution until CO$_2$ gas evolution was stopped (pH 8). The mixture was then extracted with EtOAc in a separating funnel. The organic part was then washed with saturated solution of NaHCO$_3$ (2×1 L) followed by with distilled water (2×1 L), then the organic part was dried over Na$_2$SO$_4$.

The organic part was then concentrated by rotary evaporation. The product was then purified by silica gel flash-column chromatography using puriflash column (Hex:EtOAc/1:4 to 1:9, 3 column runs, on 15 um, HC 300 g puriflash column) to obtain N$^4$-benzoyl-5'-O-(tert-butyldimethylsilyl)-3'-O-(methylthiomethyl)-2'-deoxycytidine (7) as grey powder in 60% yield.

Example 5

N$^4$-Benzoyl-3'-O-(ethyldithiomethyl)-5'-O-(tert-butyldimethylsilyl)-2'-deoxycytidine (8)

N$^4$-Benzoyl-5'-O-(tert-butyldimethylsilyl)-3'-O-(methylthiomethyl)-2'-deoxycytidine (7) (2.526 g, 5.0 mmol) dissolved in dry CH$_2$Cl$_2$ (35 mL) was added with molecular sieve-3A (10 g). The mixture was stirred for 30 minutes. It was then added with Et3N (5.5 mmol), and stirred for 20 minutes on an ice-salt-water bath. It was then added slowly with 1M SO$_2$Cl$_2$ in CH$_2$Cl$_2$ (7.5 mL, 7.5 mmol) using a syringe and stirred at the same temperature for 2 hours under N2-atmosphere. Then benzenethiosulfonic acid sodium salt (1.6 g, 8.0 mmol) in 8 mL dry DMF was added and stirred for 30 minutes at room temperature. Finally, EtSH was added (0.74 mL) and stirred additional 50 minutes at room temperature. The reaction mixture was filtered through celite-S, and washed the product out with CH$_2$Cl$_2$. After concentrating the resulting CH$_2$Cl$_2$ part, it was purified by flash chromatography using a silica gel column (1:1 to 3:7/Hex:EtOAc) to obtain compound 8 in 54.4% yield.

Example 6

N$^4$-Benzoyl-3'-O-(ethyldithiomethyl)-2'-deoxycytidine (9)

N$^4$-Benzoyl-3'-O-(ethyldithiomethyl)-5'-O-(tert-butyldimethylsilyl)-2'-deoxycytidine (8, 1.50 g, 2.72 mmol) was dissolved in 50 mL THF. Then 1M TBAF in THF (3.3 mL) was added at ice-cold temperature under nitrogen atmosphere. The mixture was stirred for 1 hour at room temperature. Then the reaction was quenched by adding 1 mL MeOH, and solvent was removed after 10 minutes by rotary evaporation. The product was purified by silica gel flash chromatography using gradient 1:1 to 1:9/Hex:EtOAc to result in compound 9. Finally, the synthesis of compound 10 was achieved from compound 9 following the standard synthetic protocol described in the synthesis of compound 5.

Figure 1:
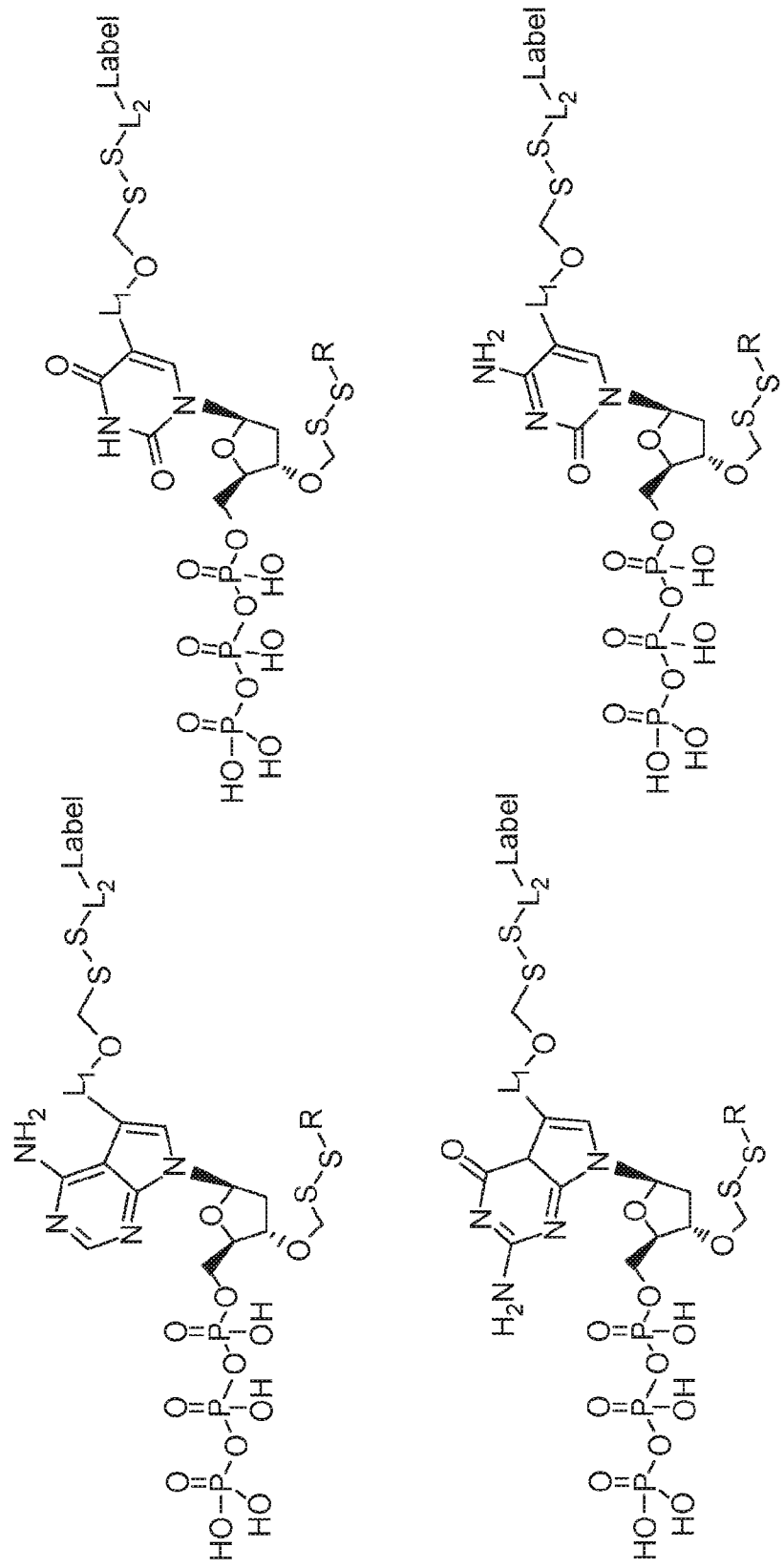
FIG. 1 shows labeled analogs of nucleotides with 3-O methylenedisulfide-containing protecting group, where labels are attached to the nucleobase via cleavable oxymethylenedisulfide linker (—OCH$_2$—SS—). The analogs are (clockwise from the top left) for deoxy adenosine, thymidine or deoxyuridine, deoxycytidine and deoxyguanosine.
Figure 2:
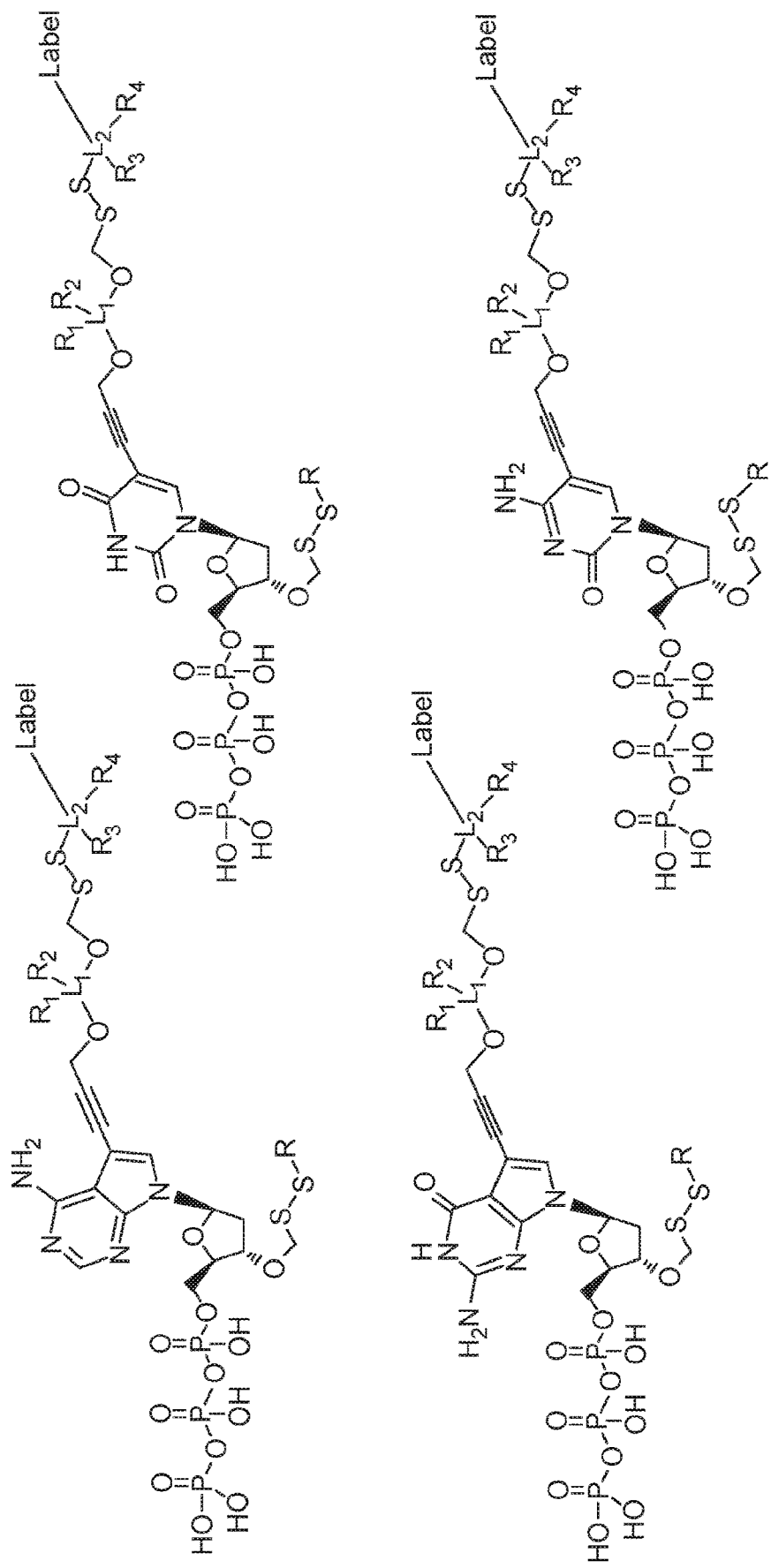
FIG. 2 shows an example of the labeled nucleotides where the spacer of the cleavable linker includes the propargyl ether linker. The analogs are (clockwise from the top left) for deoxyadenosine, thymidine or deoxyuridine, deoxycytidine and deoxyguanosine.
Figure 3:
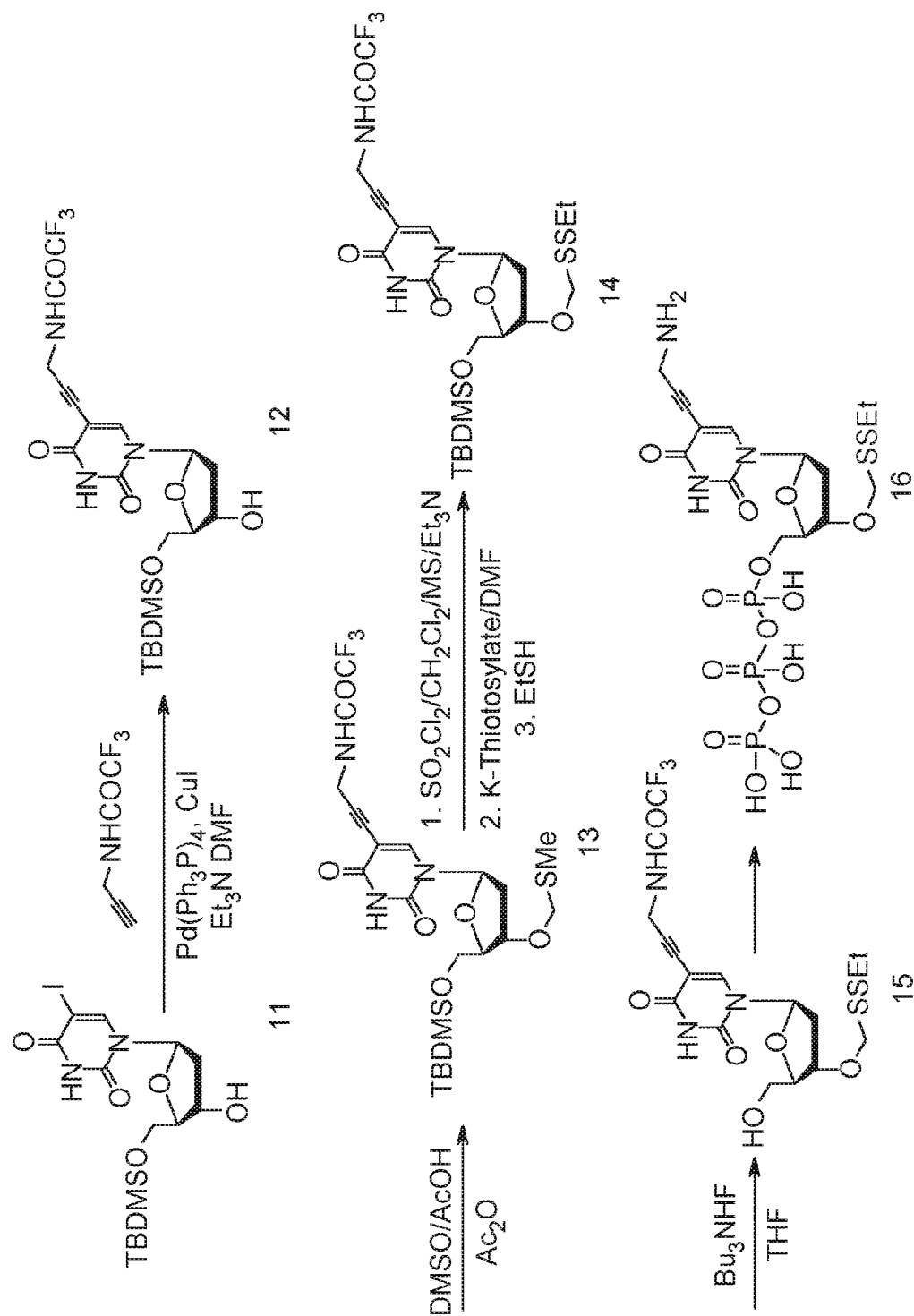
FIG. 3 shows a synthetic route of the labeled nucleotides specific for labeled dT intermediate.
Figure 4:
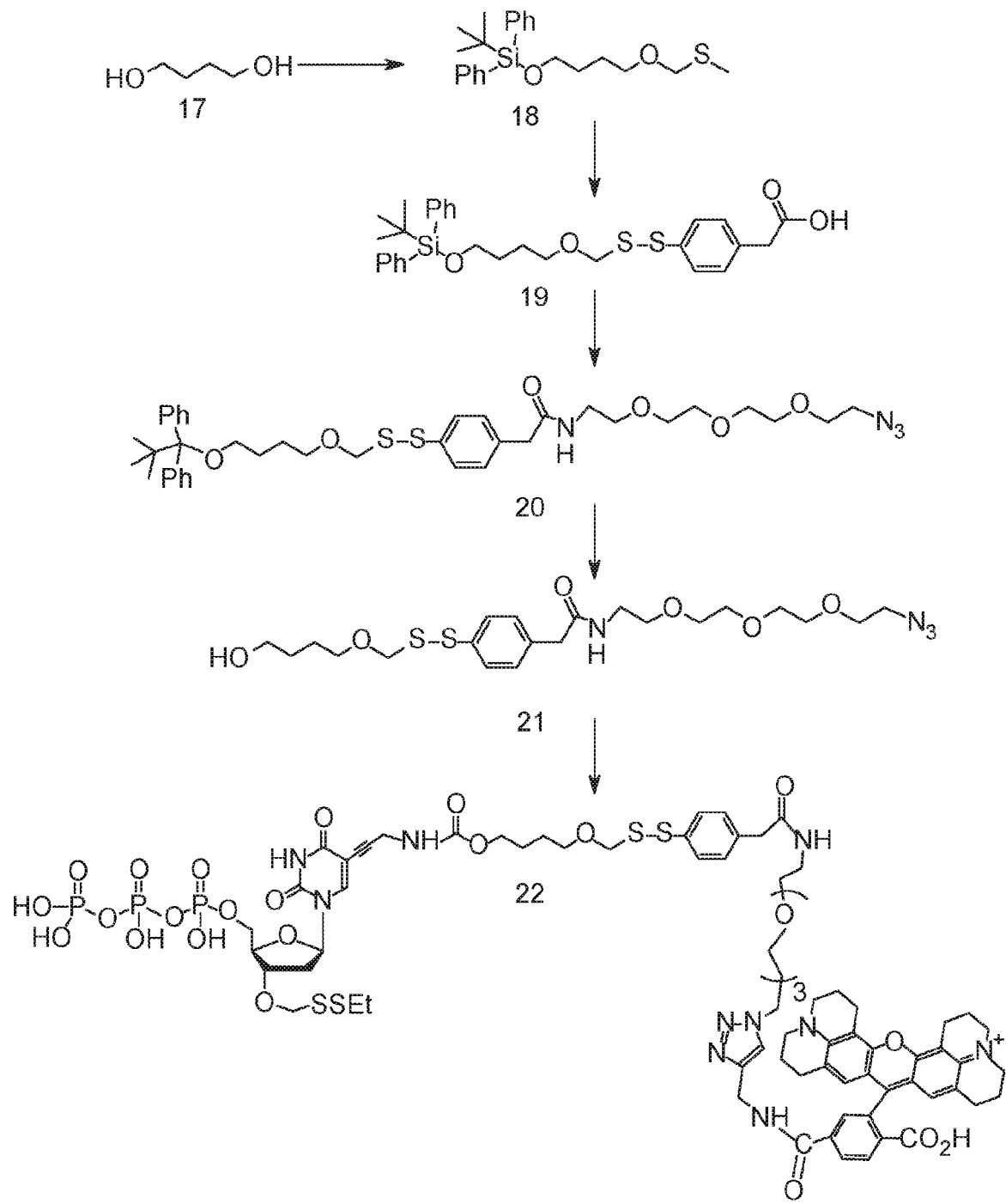
FIG. 4 shows a cleavable linker synthesis starting from an 1,4-butanediol.

The synthesis of the labeled nucleotides can be achieved following the synthetic routes shown in FIG. 3 and FIG. 4. FIG. 3 is specific for the synthesis of labeled dT intermediate, and other analogs could be synthesized similarly.

The invention claimed is:

1. A polymerase enzyme that shares at least 95% amino acid sequence identity to SEQ ID NO:1, comprising the following mutation(s): L408S, Y409G, and P410S, and wherein the polymerase enzyme has little or no 3'-5' exonuclease activity.

2. The polymerase according to claim 1, wherein the polymerase is from an organism belonging to the genera of *Pyrococcus*.

3. The polymerase according to claim 1, wherein the polymerase additionally, comprises one or more of the following additional mutations D141A, E143A.

4. The polymerase according to claim 1, wherein the polymerase additionally comprises the mutation A485L.

5. The polymerase according to claim 1, wherein the enzyme shares 98% sequence identity with SEQ ID NO: 1 and additionally has the following set of mutations, (i) L408S, Y409G, P410S and (ii) A485L.

6. The polymerase according to claim 1, wherein the enzyme has an amino acid sequence according to SEQ ID NO: 2 or SEQ ID NO: 3.

7. The polymerase according to claim 1, which exhibits an increased rate of incorporation of nucleotides which have been modified at the 3' sugar hydroxyl such that the substituent is larger in size than the naturally occurring 3' hydroxyl group compared to the control polymerase.

8. A nucleic acid molecule encoding a polymerase according to claim 1.

9. An expression vector comprising the nucleic acid molecule of claim 8.

10. A method for incorporating nucleotides which have been modified at the 3' sugar hydroxyl such that the substituent is larger in size than the naturally occurring 3' hydroxyl group into DNA, the method comprising:
  a) providing a reaction mixture comprising the following substances (i) a polymerase according to claim 1, (ii) template DNA, (iii) one or more nucleotides, which have been modified at the 3' sugar hydroxyl such that the substituent is larger in size than the naturally occurring 3' hydroxyl group, and
  b) subjecting said reaction mixture to conditions which enable the polymerase to catalyze the primer extension reaction.

11. Use of a polymerase according to claim 1 for DNA sequencing, DNA labeling, primer extension, or nucleic acid amplification, comprising:
  a) providing a reaction mixture comprising the following substances (i) a polymerase according to claim 1, (ii) template DNA, and (iii) one or more nucleotides, which have been modified at the 3' sugar hydroxyl such that the substituent is larger in size than the naturally occurring 3' hydroxyl group, and
  b) subjecting said reaction mixture to conditions which enable the polymerase to incorporate one or more nucleotides to the template DNA.

12. A kit comprising a polymerase according to claim 1.

* * * * *